US008100966B2

(12) United States Patent
Steinhardt et al.

(10) Patent No.: US 8,100,966 B2
(45) Date of Patent: Jan. 24, 2012

(54) AUDITORY OSSICLE PROSTHESIS WITH VARIABLE COUPLING SURFACES

(75) Inventors: Uwe Steinhardt, Hirrlingen (DE); Heinz Kurz, Dusslingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 256 days.

(21) Appl. No.: 12/383,003

(22) Filed: Mar. 18, 2009

(65) Prior Publication Data

US 2009/0240330 A1 Sep. 24, 2009

(30) Foreign Application Priority Data

Mar. 20, 2008 (DE) ........................ 10 2008 015 117

(51) Int. Cl.
*A61F 2/18* (2006.01)

(52) U.S. Cl. ........................................................ 623/10

(58) Field of Classification Search . 623/10; *A61F 2/06*
See application file for complete search history.

(56) References Cited

U.S. PATENT DOCUMENTS

| | | | |
|---|---|---|---|
| 4,601,723 | A | 7/1986 | McGrew |
| 6,168,625 | B1 | 1/2001 | Prescott |
| 6,432,139 | B1 | 8/2002 | Elies et al. |
| 6,554,861 | B2 | 4/2003 | Knox et al. |
| 6,579,317 | B2 | 6/2003 | Kurz |
| 2002/0045939 | A1 | 4/2002 | Kurz |
| 2004/0162614 | A1 | 8/2004 | Steinhardt et al. |

(Continued)

FOREIGN PATENT DOCUMENTS

DE 1 926 587 7/1970

(Continued)

OTHER PUBLICATIONS

U.S. Appl. No. 12/383,005, Applicant: Uwe Steinhardt et al., filed Mar. 18, 2009 entitled Auditory Ossicle Prosthesis With Variable Coupling Surfaces.

(Continued)

*Primary Examiner* — Thomas J Sweet
*Assistant Examiner* — Seema Swaminathan
(74) *Attorney, Agent, or Firm* — Flynn, Thiel, Boutell & Tanis, P.C.

(57) ABSTRACT

An auditory ossicle prosthesis (10) which comprises, at one end, a plate-shaped first securing element (11) for bearing on the tympanic membrane or on the footplate of the stirrup, and, at its other end, a second securing element (12) for mechanical connection to the ossicular chain or to the inner ear, and also a connection element (13) that connects the two securing elements so as to conduct sound, wherein the first securing element has a radially inner coupling area (14) for coupling the first securing element to the connection element, and also a plurality of web elements (15, 15', 15") for radial connection of the coupling area to radially outer portions (16, 16') of the first securing element, is characterized in that the coupling area and/or the web elements and/or the radially outer portions are of such a geometric configuration that they together form pieces of a jigsaw from which the first securing element can be assembled in its entirety, wherein the individual jigsaw pieces can be joined to one another or removed from one another, and wherein the first securing element is inherently mechanically stable in the state with the jigsaw pieces joined together. This means that the number of different prostheses to be kept ready during an operation can be reduced to a single standard prosthesis, without losing the possibility of optimal adaptation of the prosthesis to the specific case of use.

30 Claims, 27 Drawing Sheets

11

U.S. PATENT DOCUMENTS

| | | | |
|---|---|---|---|
| 2006/0271190 | A1 | 11/2006 | Reitan et al. |
| 2008/0234817 | A1 | 9/2008 | Huettenbrink et al. |
| 2009/0164010 | A1 | 6/2009 | Steinhardt et al. |

FOREIGN PATENT DOCUMENTS

| | | | |
|---|---|---|---|
| DE | 197 44 789 | A1 | 4/1998 |
| DE | 298 02 776 | U1 | 4/1998 |
| DE | 19647579 | A1 * | 5/1998 |
| DE | 299 04 770 | U1 | 7/1999 |
| DE | 10 2007 013 708 | B3 | 1/2008 |
| DE | 20 2007 012 217 | U1 | 1/2008 |
| DE | 10 2007 062 151 | B3 | 12/2008 |
| EP | 1 181 907 | B1 | 2/2002 |
| WO | WO 02/069850 | A1 | 9/2002 |

OTHER PUBLICATIONS

U.S. Appl. No. 12/383,004, Applicant: Uwe Steinhardt et al., filed Mar. 18, 2009 entitled Auditory Ossicle Prosthesis With Variable Coupling Surfaces.

Yung, M.W., Brewis, C., "A comparion of the user-friendliness of hydroxyapatite and titanium ossicular prostheses", *The Journal of Laryngology & Otology*, Feb. 2002, vol. 116, pp. 97-102.

European Search Report dated Sep. 28, 2009 for European Application No. 09 00 3856 (4 pages).

U.S. Appl. No. 12/313,388, Applicant: Uwe Steinhardt et al, filed Nov. 20, 2008 entitled Modular Total Prosthesis for The Middle Ear.

* cited by examiner

AUDITORY OSSICLE PROSTHESIS WITH VARIABLE COUPLING SURFACES

BACKGROUND OF THE INVENTION

The invention relates to an auditory ossicle prosthesis which replaces or spans at least one member or parts of one member of the ossicular chain, wherein the auditory ossicle prosthesis comprises, at one end, a substantially plate-shaped first securing element for bearing on the tympanic membrane or on the footplate of the stirrup, and, at its other end, a second securing element for mechanical connection to a member or parts of a member of the ossicular chain or to the inner ear, and also a connection element that connects the two securing elements to each other so as to conduct sound, and wherein the plate-shaped first securing element has a radially inner coupling area for mechanically coupling the first securing element to the connection element and also a plurality of web elements for radial connection of the radially inner coupling area to radially outer portions of the first securing element.

A device of this kind is known from DE 10 2007 013 708 B3.

Auditory ossicle prostheses are used to transmit sound or a sound signal from the tympanic membrane to the inner ear when the ossicles of the human middle ear are entirely or partially absent or damaged. The auditory ossicle prosthesis has two ends, and, depending on the specific circumstances, one end of the auditory ossicle prosthesis is secured to the tympanic membrane, for example by means of a headplate, and the other end of the auditory ossicle prosthesis is secured, for example, to the stirrup of the human ossicular chain or plunged directly into the inner ear. With the known auditory ossicle prostheses, the sound conduction or signal transmission between the tympanic membrane and the inner ear is often made possible only to a limited extent, since these prostheses are able only to an extremely limited extent to replace the natural anatomical features of the ossicular chain.

After the prosthesis has been placed surgically in the middle ear and the tympanic membrane has been closed again, the so-called incorporation phase starts. During this period, scars and tissue strands form and generate unpredictable forces, which can lead to the prosthesis shifting from its local position. In the case of a stiff connection between headplate and shaft, increased pressure peaks can occur between the edge of the headplate and the tympanic membrane or the transplant between tympanic membrane and headplate. These pressure peaks can be so high as to result in penetration or extrusion through the tympanic membrane. For this reason, it is very useful if, after the operation, the prosthesis has a certain degree of mobility and flexibility, such that the headplate is able to automatically adapt itself to the position of the tympanic membrane after the operation.

Since the anatomical features of the ear, for example the position, shape and size of the stirrup, anvil, hammer and tympanic membrane, also vary between individuals, it is very advantageous if auditory ossicle prostheses are not made rigid, but instead have a certain flexibility or variability.

To achieve this flexibility or variability, various securing and coupling devices for auditory ossicles are known that have elastic parts and/or hinges. Such a hinged connection between a securing element, mounted on the footplate of the stirrup, and the elongate shaft is described in EP 1 181 907 B1 and is offered by the Applicant under the brand name "Ball-Joint".

Another complication that occurs occasionally is the result of insufficient air in the middle ear cavity and of associated acute or chronic inflammations, tumor formations, adhesions in the region of the tympanic membrane and stiffening of the latter. In cases of dysfunction of the Eustachian tube, for example, an underpressure may develop in the middle ear and cause eversion or so-called retraction of the tympanic membrane, with resulting adhesion to the stirrup, for example. To counteract this and to be able to follow the postoperative movements of the tympanic membrane, the headplates in known auditory ossicle prostheses are designed to be able to tilt relative to the connection element that connects the headplate to the second securing element and that is in most cases designed as an elongate shaft. A headplate of this kind, which is inherently rigid but is able to tilt relative to the connection element, is described inter alia in US 2004/0162614 A1, in the article by M. W. Yung, Ph.D, F.R.C.S, D.L.O. and C. Brewis, F.R.C.S. entitled "A comparison of the user-friendliness of hydroxyapatite and titanium ossicular prostheses" in the Journal of Laryngology & Otology, February 2002, volume 116, pages 97-102, or, for example, also in US 2006/0271190 A1.

However, a disadvantage of these known auditory ossicle prostheses is that, in the event of local medial movements of the tympanic membrane, the inherently rigid tilting of the headplate means that the opposite side of the headplate is also moved out laterally at the same time, as a result of which pressure peaks are generated on the tympanic membrane.

In order to achieve a high level of postoperative flexibility and variability of the prosthesis, while at the same time considerably improving the quality of the sound conduction through the prosthesis, without causing the above-mentioned complications to occur, the aforementioned document DE 10 2007 013 708 B3 proposes that the web elements are of such a geometric configuration that, in the event of local medial movement of the tympanic membrane, they are able to follow this medial movement locally, but do not transmit the movement to remote areas of the headplate. In the event of a slight medial movement of the tympanic membrane, this flexible configuration of the auditory ossicle prosthesis avoids rigid tilting of the whole headplate. Instead, the headplate twists upon itself locally but, in the event of movements of the tympanic membrane caused by sound, it nevertheless transmits these movements to the connection element, such that an optimal transmission of the sound or of the sound signal from the tympanic membrane to the middle ear and onward to the inner ear is ensured.

This provides a very considerable improvement over the rest of the known prior art. Unfortunately, however, further problems still persist that cannot be solved by these measures alone:

In the context of a tympanoplasty procedure in the human middle ear, the pathology and anatomy may necessitate very different kinds of structural reconstructions that are specific to each individual patient. Depending on the extent and shape of any parts of the middle ear anatomy that are still present and that are perhaps partially intact, for example the hammer (malleus), the anvil (incus), the stirrup (stapes) or the tympanic membrane, the middle ear prostheses to be implanted need to have a correspondingly large number of different geometries, some of them differing quite considerably in shape and size.

Since, before the start of surgery of the middle ear, it cannot be predicted, or can be predicted only with great difficulty (only roughly if at all, and practically never exactly), how the subsequent reconstruction of the tympanic membrane and of the ossicular chain will turn out in the course of the operation, a very large number of middle ear prostheses with different geometries, shapes and sizes have to be kept ready for each operation that is to be performed, so as to ensure that the surgeon can at all times select the most suitable prosthesis during the operation, that is to say the prosthesis allowing him to deal with the specific case in question. Otherwise, it may not be possible to guarantee optimal treatment.

Another factor is that said problems of adapting the auditory ossicle prosthesis during surgery may occur not only in the area where the first securing element bears on the tympanic membrane, but also in the area of a likewise plate-shaped second securing element which may be required to allow the prosthesis to bear on the footplate of the stirrup. Particularly for the area of a total reconstruction toward the inner ear, a total prosthesis for this purpose normally has a stamp with a standard diameter of 0.8 mm. Surgeons often express the wish that different surface areas could be made available, depending on the intraoperative situation, to be placed onto the footplate of the stirrup. This desire among specialists would be satisfied by provision of an additional securing element which is connected or can be connected to the stamp and which, in terms of the size of its surface, would be able to be varied within wide limits.

If the auditory ossicle prosthesis is not a total prosthesis, and the first securing element is therefore not designed as a headplate for bearing on the tympanic membrane, but instead as a clip for securing the prosthesis on a member of the ossicular chain, the described problems of adaptation occur exclusively at the inner ear end of the auditory ossicle prosthesis.

A further problem is that, throughout the world, extremely different surgical techniques are employed, which postulate different types of reconstructions in the middle ear. These require suitably adapted middle ear prostheses which differ greatly from one another in size and shape and which again have to be kept ready during each operation in order to allow the surgeon to employ what he considers to be the best method in each particular case.

SUMMARY OF THE INVENTION

In light of this, the object of the present invention is to improve a middle ear prosthesis of the type described above by the simplest possible technical means and at minimal cost, such that the number of different prostheses to be kept ready during an operation can be considerably reduced, preferably to a single standard prosthesis, without in so doing losing the possibility of optimal adaptation of the prosthesis in each particular case.

According to the invention, this object is achieved in a surprisingly simple and effective way, by virtue of the fact that the coupling area and/or the web elements and/or the radially outer portions are of such geometric configuration that they together form pieces of a jigsaw from which the plate-shaped first securing element can be assembled in its entirety, wherein the individual jigsaw pieces can be joined to one another or removed from one another, and wherein the first securing element is inherently mechanically stable in the state with the jigsaw pieces joined together.

The plate-shaped first securing element of the middle ear prosthesis according to the invention can be designed, for example, as a headplate placed against the tympanic membrane in the context of a tympanoplasty procedure and is constructed such that it is variable within very wide limits in terms of its shape and surface. During surgery, the prosthesis according to the invention, kept ready as a standard prosthesis, can thus be reconfigured very easily, very flexibly and in an extremely targeted manner that meets the situation particular to a specific patient.

Simple ad hoc changes can be made to the standard prosthesis according to the invention, for example to the angles, lengths or surface areas, to serve the purpose of greatly improved adaptation to each particular case. Thus, the middle ear prosthesis according to the invention affords the operating surgeon an extremely high degree of variation and flexibility, without the previous requirement to keep in stock a large number of very different prosthesis shapes, sizes and geometries. It is thus possible for the surgeon, during the operation, to make specific changes to the prosthesis that allow him to adapt or adjust the prosthesis specifically to the particular set of circumstances.

By means of the jigsaw technique used according to the invention, it is quite simple to change, for example, the size of the headplate of the prosthesis such that it touches only very specific areas of the tympanic membrane, generally those that are known to play an essential role in acoustic transmission.

It often happens that the manubrium is present on the tympanic membrane, or indeed that it is missing, depending on how many previous operations have been performed, which operating method was employed and which specific measure was taken. Accordingly, a headplate configured according to the invention with a variable surface allows the operating surgeon to react precisely and correctly, i.e. allows the area responsible for the manubrium to be detached or, if need be, joined.

A similar situation also applies to the coupling of the auditory ossicle prosthesis to the footplate of the stirrup, where the inventive surface-variable design of the corresponding plate-shaped securing element is likewise able to offer a hitherto unknown intraoperative flexibility in terms of optimal adaptation to the situation presented by the individual patient.

The radially inner coupling area can be arranged centrally around the area centroid of the plate-shaped first securing element.

The basic concept according to the invention can be doubly exploited if both securing elements are plate-shaped and constructed from jigsaw pieces, wherein the first securing element serves as a flat headplate for mechanical connection to the tympanic membrane, and the second securing element is designed to allow the auditory ossicle prosthesis to bear on the footplate of the stirrup.

Another advantageous embodiment of the auditory ossicle prosthesis according to the invention is characterized in that at least one radially innermost jigsaw piece is provided which contains the coupling area, and in that at least one radially outer jigsaw piece forms a ring surrounding the radially innermost jigsaw piece in the state when they are joined together. Generally, several radial sequences of jigsaw rings will be provided. In this way, as when peeling an onion, the surface of the first securing element can be reduced to a desired size depending on the actual circumstances by removing a corresponding number of radially outer jigsaw rings. Moreover, by attaching the outer jigsaw ring last removed, a securing element that has been made too small can also be enlarged again, which further increases the degree of flexibility available to the operating surgeon.

Embodiments of the invention are also preferred in which at least one jigsaw piece is provided which can be joined from the side onto at least one other jigsaw piece at the outer edge of the plate-shaped first securing element. This opens up a huge number of design possibilities in terms of the geometric shape of the securing element. In particular, it is now no longer essential to implant symmetrical shapes, as were required hitherto with the available standard prostheses. Instead, the operating surgeon is easily able, during the operation, to produce by hand an optimally adapted auditory ossicle prosthesis that is tailor-made to the situation.

In advantageous developments of this class of embodiments, the jigsaw piece that can be joined on from the side is shaped as an appendix for the hammer or the manubrium of the auditory ossicle prosthesis and, in the state when joined together, protrudes radially outward from the edge of the plate-shaped first securing element.

These developments can be further improved by the fact that the jigsaw piece that can be joined on from the side is anchored resiliently in the first securing element, which in particular makes inadvertent breaking-off of the very fine miniature part upon joining to the securing element very difficult.

The resilient anchoring of the jigsaw piece can be achieved by means of a simple clip element, for example.

In other advantageous variants, the jigsaw piece that can be joined on from the side is anchored in the first securing element with a snap-fit action and thus secure against loss.

One class of embodiments of the invention is characterized in that, in the state with the jigsaw pieces joined together, the plate-shaped first securing element has apertures that extend through the plane of the plate. In this way it is also easy to achieve the above-mentioned asymmetrical configurations of the geometry of the securing element. Moreover, because of the apertures, the plate-shaped securing element has a high degree of flexibility with respect to local movements of parts of the securing element out from the plane of the plate, which is particularly advantageous especially in embodiments of the securing element as a headplate for bearing on the tympanic membrane.

In an alternative class of embodiments, the plate-shaped first securing element, in the state with the jigsaw pieces joined together, forms an inherently closed surface and has no apertures extending through the plane of the plate. By virtue of the design, the securing element is particularly stiff against torsion.

An embodiment of the auditory ossicle prosthesis is very particularly preferred in which the radially outer portions of the plate-shaped first securing element form an outer ring area. This embodiment is suitable in particular for the above-mentioned rapid and successive “onion peeling” reduction of the surface of the first securing element radially from the outside inward.

One group of developments of this embodiment is characterized in that the radially outer ring area is uninterrupted and closed. In this way, by removing whole ring areas, the surface of the securing element can be made symmetrically smaller, radially from the outside inward. Moreover, in the case of postoperative retractions, it is in this way possible to avoid the formation of dangerous points directed at the tympanic membrane.

As an alternative to this, in another group of developments, the radially outer ring area has at least one interruption, preferably several interruptions. In this way, in particular, asymmetrical shapes can be easily produced.

In developments of the embodiment described above, the radially outer ring area can have an oval or circular shape, which is known per se from the prior art and will generally constitute the standard version of the auditory ossicle prosthesis according to the invention.

To make the auditory ossicle prosthesis easier to implant surgically, in a special variant the radially outer ring area can have a unilateral recess for receiving the manubrium.

In another variant, the radially outer ring area of the plate-shaped first securing element has a bulge that extends radially outward in the plane of the plate and that is able to engage in structures of the ossicular chain.

However, a variant is also possible in which the radially outer ring area has an undulating outer contour, which proves favorable in specific geometric situations in the middle ear, of the kind that may often be found in practice in the patient.

Another embodiment of the auditory ossicle prosthesis according to the invention is characterized in that the web elements between the radially inner coupling area and the radially outer portions of the plate-shaped first securing element are uninterrupted, so as to increase the desired flexibility mentioned above.

Alternatively, however, at least some web elements can also have an interruption between the radially inner coupling area and the radially outer portions of the plate-shaped first securing element, which increases the flexibility in terms of the securing element twisting in the plane of its plate.

Embodiments of the invention are particularly preferred in which the web elements of the plate-shaped first securing element are not rectilinear in the plane of the plate but instead extend in several curves, thus further strengthening the desired effect of local flexibility of a tympanic membrane headplate and of only locally limited deflection in the event of slight medial movements of the tympanic membrane. Moreover, in this way a headplate can more easily follow any postoperative change of the tympanic membrane.

In other advantageous embodiments of the auditory ossicle prosthesis according to the invention, each web element is connected to at least two other web elements, resulting in a kind of flexible network of web elements.

It is particularly expedient if the web elements have a maximum width b and the radially outer ring area has a maximum width B, where $2b<B$.

In order to achieve the desired flexibility in the case of a maximum width b of the web elements and a minimum diameter D of the plate-shaped first securing element, including the ring area, the following should apply: $b \leqq 0.05$ D, preferably $b \approx 0.03$ D. In the prior art, for example in the auditory ossicle prostheses described in US 2004/0162614 A1, the ratio b/D is at least 0.1 or above.

It is also expedient if the plate-shaped first securing element of the auditory ossicle prosthesis according to the invention has a thickness, in particular a plate thickness t of between 0.01 mm and 0.5 mm, preferably of between 0.1 mm and 0.25 mm, and a minimum diameter D of between 1.5 mm and 8 mm, preferably of between 2 m and 5 mm, and the web elements have a maximum width b of between 0.01 mm and 0.3 mm, preferably of between 0.05 mm and 0.2 mm.

In the auditory ossicle prosthesis according to the invention, the connection element between the securing elements is generally designed as an elongate shaft, as is well known per se from the prior art.

In order to increase the above-mentioned flexibility and variation of the prosthesis, as is described per se in EP 1 181 907 B1, it is possible, in a particularly preferred development of this embodiment, to provide at least one ball joint on or in the elongate shaft. Variants in which the elongate shaft comprises a large number of further rotation elements adjoining one another, preferably as a ball joint chain, are advantageous in terms of a high degree of postoperative mobility of the prosthesis.

Alternatively, however, in particularly simple and inexpensive embodiments of the prosthesis according to the invention, the shaft can also be made in one piece and be particularly rigid.

Depending on the individual defect that is to be remedied in a patient by use of the auditory ossicle prosthesis according to the invention, or that is at least to be alleviated in terms of its effects, the construction of the prosthesis is designed accordingly. In many embodiments of the invention used in practice, the first securing element will comprise a headplate designed to bear on the tympanic membrane. In many other embodiments, for example, the prosthesis can be secured at one end to the process of the anvil and at the other to the stirrup, or it can be plunged directly into the inner ear. In this connection, an advantageous design is one in which the auditory ossicle prosthesis is located at the end point of the hammer (umbo) or directly next to it, as a result of which the maximum lever action is achieved for mechanically transmitting sound through movements in the artificial or natural ossicular chain.

One class of embodiments of the auditory ossicle prosthesis according to the invention is distinguished by the fact that the second securing element is formed as a plate, as a sleeve, as a loop, as a closed bell, as a singly or multiply slit bell or as a clip for mechanical connection to a further member of the ossicular chain.

In developments of these embodiments, the prosthesis is secured on the one hand to the tympanic membrane by way of the first securing element designed as headplate and on the other hand to the anvil or to the stirrup by way of the second securing element.

In alternative embodiments, provision may be made that the auditory ossicle prosthesis is at one end coupled directly to the inner ear, in particular via a plunger, by means of perforation of the footplate of the stirrup (stapedectomy or stapedotomy) and/or by means of opening the human cochlea (cochleotomy).

Embodiments of the invention are possible in which the prosthesis or parts thereof is/are made of biocompatible plastics, in particular silicone, polytetrafluoroethylene (PTFE) or polyether ether ketone (PEEK) and/or composite fiber materials, in particular carbon fibers. Post-operative rejection reactions can in most cases be avoided using these materials.

The auditory ossicle prosthesis according to the invention or parts thereof can be made of titanium and/or of gold and/or of tantalum and/or of steel and/or of an alloy of said metals. In addition to its strength and excellent sound conduction properties, the material titanium in particular also has excellent biocompatibility in the middle ear in humans.

In view of the above-mentioned post-operative adjustment of position, embodiments of the invention are advantageous in which the prosthesis or parts thereof, in particular one of the securing elements, is made of a material with shape memory or with superelastic properties, preferably nitinol, which is known per se from, for example, WO 02/069850 A1 or U.S. Pat. No. 6,554,861 B2.

In further embodiments, parts of the auditory ossicle prosthesis can alternatively or additionally be made from a ceramic material.

In addition to the post-operative change of position, a further problem also arises after implantation of auditory ossicle prostheses. This is due to the fact that the middle ear of the human body constitutes a "semi-open bearing". Any implantation material introduced into the body, in the context of a reconstruction of the middle ear and of its structures, is therefore subject to a particular stress arising from the fact that it lies in a contaminated and infected environment, which generally attacks the material. Since the aim of implanting an auditory ossicle prosthesis must be that the implant remains in the patient's middle ear for as long as possible and without complications, a protracted attack of the material can lead to damage of the prosthesis and/or to local infection. Both consequences are unacceptable. To prevent damage of the implanted material and also of the surrounding tissue on a permanent basis, another particularly preferred embodiment of the invention involves a biologically active coating, in particular a coating that inhibits growth and/or promotes growth and/or has an antibacterial action, being provided at least in some areas of the surface of the auditory ossicle prosthesis.

In the auditory ossicle prosthesis according to the invention, a securing element designed as headplate should in principle have a coating that promotes growth, whereas a securing element leading directly into the ear, and designed in the form of a plunger for example, should have a coating that inhibits growth.

An embodiment of the auditory ossicle prosthesis according to the invention is particularly preferred in which the weight distribution of the individual parts of the prosthesis is calculated as a function of a desired, predefinable frequency response of the sound conduction in the middle ear. It is thus possible, without major additional technical outlay, to achieve a degree of mechanical tuning of the sound propagation properties by means of an individually configured auditory ossicle prosthesis.

Such a tuning effect can be achieved, in particular embodiments, by the fact that at least one additional weight is secured on a part of the ossicular chain or of the prosthesis as a function of a desired, predefinable frequency response of the sound conduction in the middle ear. In advantageous developments of these embodiments, the additional weight is secured on a part of the ossicular chain or the prosthesis by means of a clip. In addition, the additional weight and/or the clip can also be coated with a biologically active coating.

A further embodiment of the invention, finally, is distinguished by the fact that the prosthesis is connected to an active vibration part of an active, in particular implantable hearing aid. In this way, extensive hearing damage can also be largely remedied by application of modern electronics or can at least be substantially alleviated in terms of its effects, in which case, on account of the above-described coating, a physical connection of the prosthesis to the outside world does not cause any problems resulting from increased bacterial ingress into the area of the middle ear, if the coating is made suitably antibacterial.

Further features and advantages of the invention will become clear from the following detailed description of illustrative embodiments of the invention, from the figures in the drawing, which shows important details of the invention, and also from the claims. The individual features can each be realized singly or in any desired combinations in variants of the invention.

Illustrative embodiments of the invention are depicted in the schematic drawing and are explained in more detail in the following description.

BRIEF DESCRIPTION OF THE DRAWINGS

The figures of the drawing are divided into groups of three, the respective individual figures of a group being distinguished from one another by a number followed by a, b or c. The "a" figures in each case show a schematic perspective view of an embodiment of the auditory ossicle prosthesis according to the invention; the "b" figures show the first securing element from the "a" figure, and designed according to the invention, in the assembled state of the jigsaw pieces; and the "c" figures show the first securing element from the corresponding "b" figure in the state when the jigsaw pieces are disassembled. Moreover, elements having the same structure and/or the same function are identified by the same reference number in the drawing.

DESCRIPTION OF THE PREFERRED EMBODIMENTS

Figure 1A:
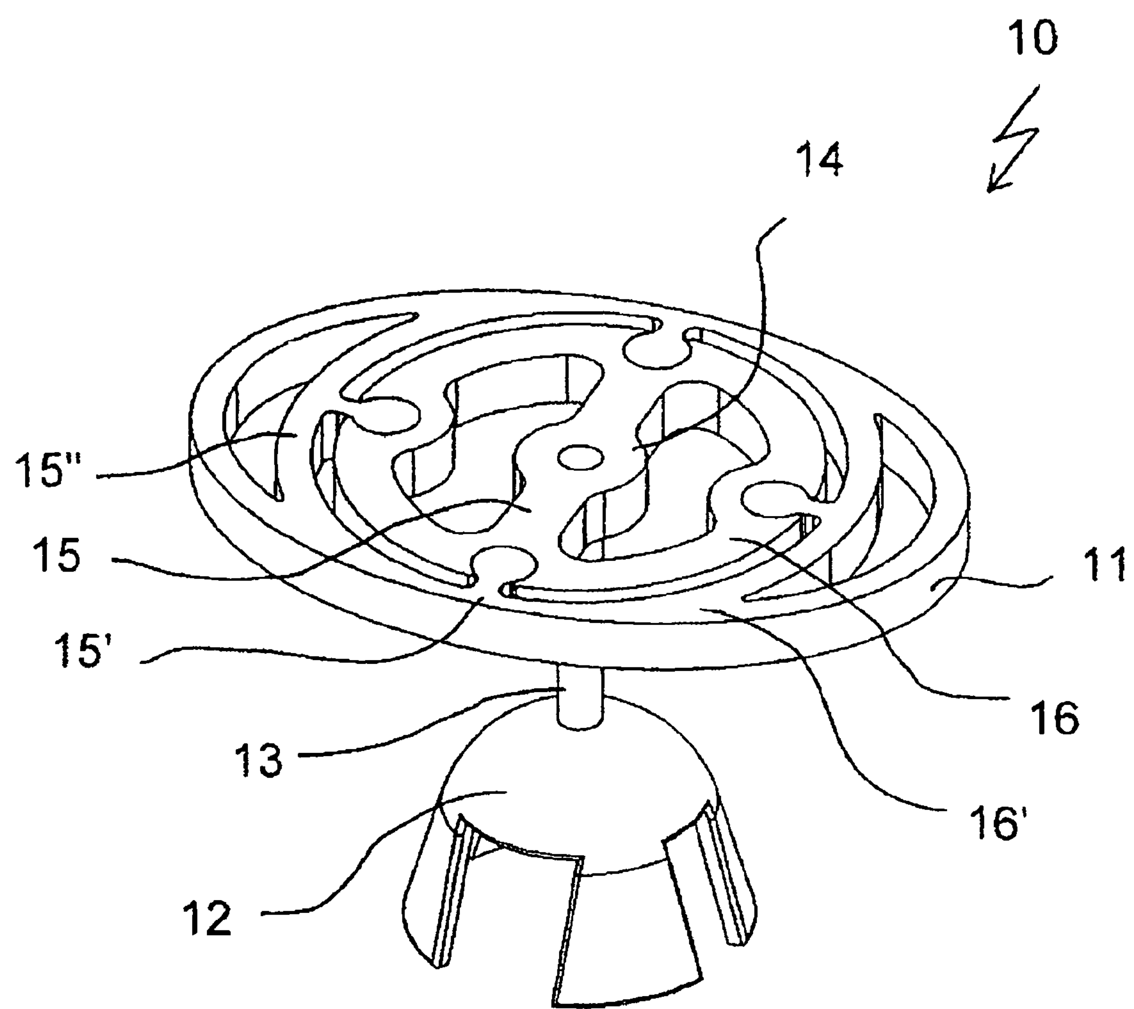
FIGS. 1*a-c* show an embodiment of the auditory ossicle prosthesis according to the invention with a first securing element which is designed as a tympanic membrane headplate and has an annular structure, and with a second securing element designed as a slotted bell at the other end of the connection element.

The auditory ossicle prostheses 10; 20; 30; 40; 50; 60; 70; 80; 90 according to the invention each have, at one end, a plate-shaped first securing element 11; 21; 31; 41; 51; 61; 71; 81; 91 which is designed in the form of a headplate for bearing on the tympanic membrane or as a footplate for bearing on the footplate of the stirrup. At the other end of the auditory ossicle prostheses 10; 20; 30; 40; 50; 60; 70; 80; 90, there is a second securing element 12; 22; 32; 92 for mechanical connection of the prosthesis to a member or parts of a member of the ossicular chain or directly to the inner ear. Arranged between these is a connection element 13; 23; 93 which connects the two securing elements to each other so as to conduct sound and which, in the embodiments shown, is designed in the form of a one-part or multi-part, short or long shaft.

The plate-shaped first securing element 11; 21; 31; 41; 51; 61; 71; 81; 91 in each case has a radially inner coupling area 14; 24; 34; 44; 54; 64; 74; 84; 94, arranged around its area centroid, for mechanically coupling the first securing element to the connection element 13; 23; 93, and also a plurality of web elements 15, 15', 15''; 25, 25', 25''; 35, 35', 35'', 35'''; 45, 45'; 55, 55', 55''; 65, 65'; 75, 75', 75''; 85, 85'; 95, 95' for radial connection of the radially inner coupling area to radially outer portions 16, 16'; 26, 26'; 36, 36'; 46, 46'; 56, 56'; 66, 66'; 76, 76'; 86, 86'; 96, 96' of the first securing element 11; 21; 31; 41; 51; 61; 71; 81; 91.

The coupling area 14; 24; 34; 44; 54; 64; 74; 84; 94 and/or the web elements 15, 15', 15''; 25, 25', 25''; 35, 35', 35'', 35'''; 45, 45'; 55, 55', 55''; 65, 65'; 75, 75', 75''; 85, 85'; 95, 95' and/or the radially outer portions 16, 16'; 26, 26'; 36, 36'; 46, 46'; 56, 56'; 66, 66'; 76, 76'; 86, 86'; 96, 96' are of such a geometric configuration that they together form pieces of a jigsaw from which the plate-shaped first securing element 11; 21; 31; 41; 51; 61; 71; 81; 91 can be assembled in its entirety, wherein the individual jigsaw pieces can be joined to one another or removed from one another, and wherein the first securing element 11; 21; 31; 41; 51; 61; 71; 81; 91 is inherently mechanically stable in the state with the jigsaw pieces joined together.

Figure 1B:
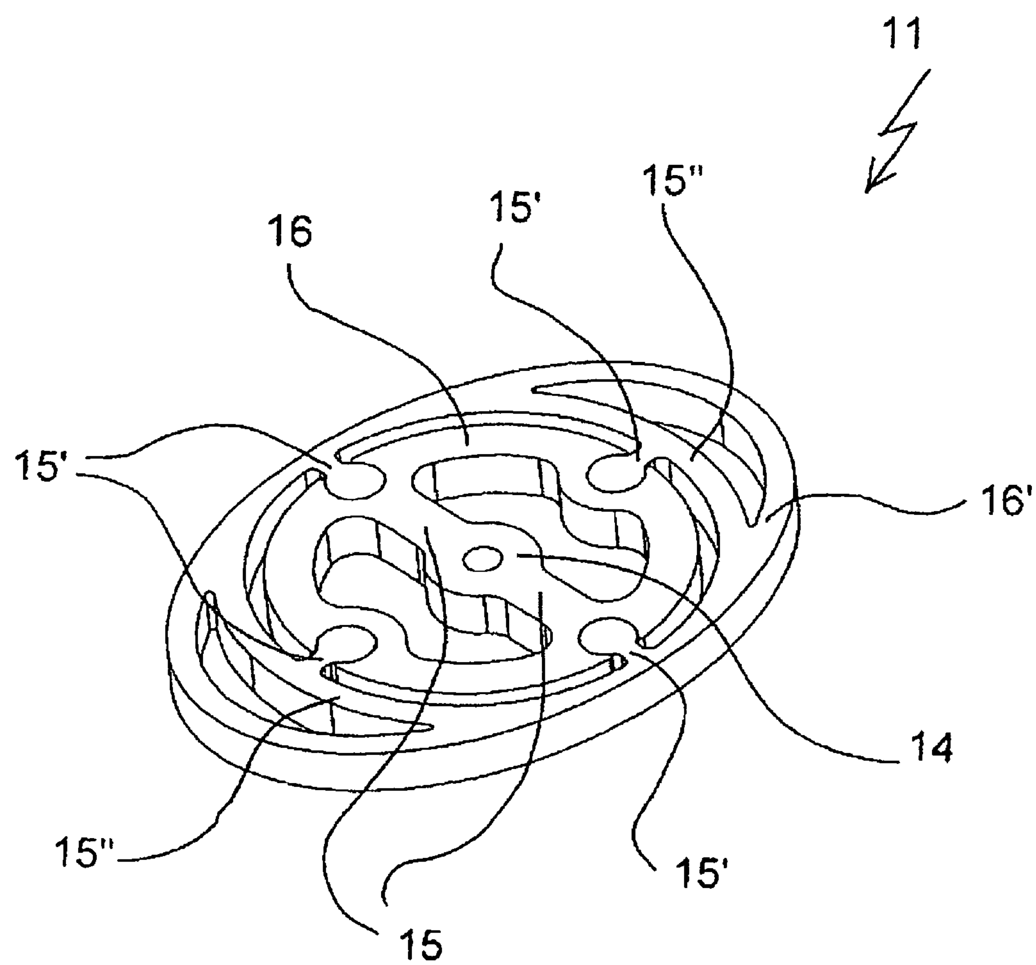
Figure 1C:
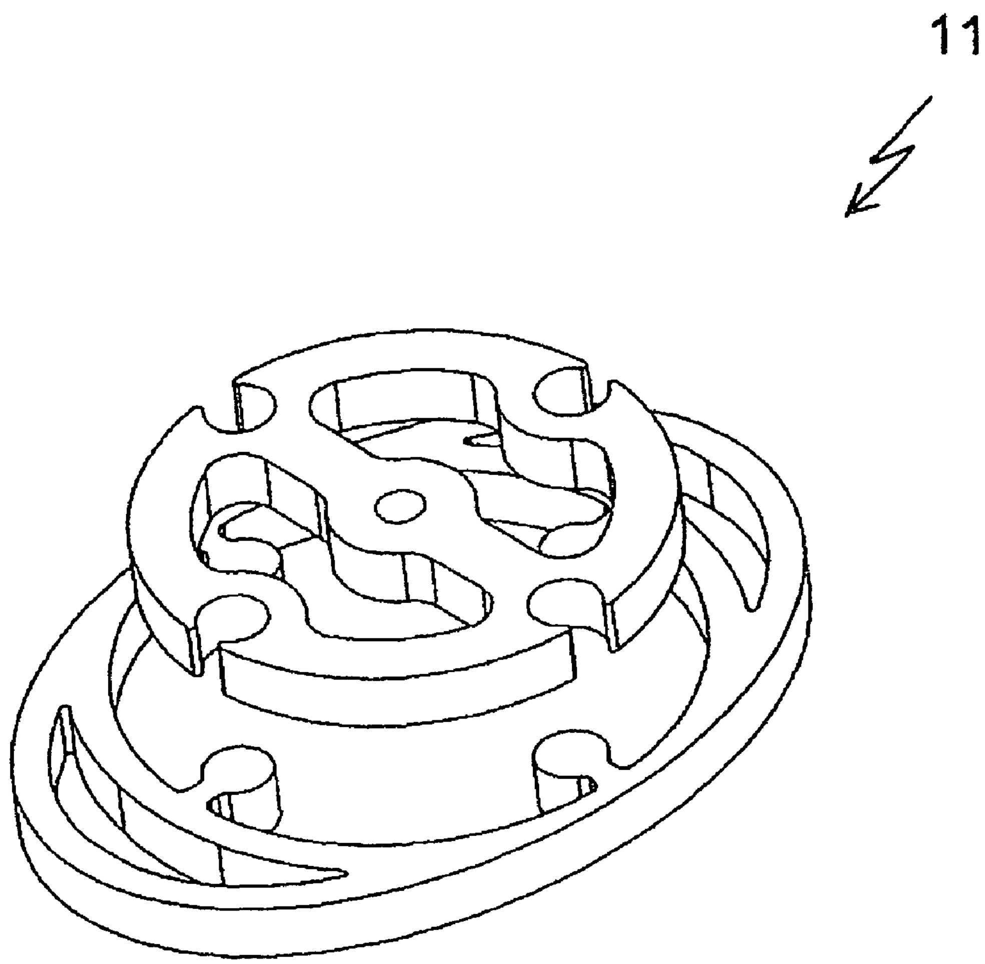

The embodiment shown in FIGS. 1*a-c* has a headplate as first securing element 11, a short, rigid one-piece shaft as connection element 13, and a second securing element 12 with a bell-shaped configuration which is used to secure the auditory ossicle prosthesis 10 to a member of the ossicular chain, for example to the anvil or to the stirrup. The first securing element 11 has apertures extending through the plane of the plate in order to increase the flexibility of the headplate when twisting in and out of the plane of the plate, and it comprises a radially inner jigsaw piece 16 that contains the coupling area 14. A radially outer jigsaw piece 16' forms a ring surrounding the radially inner jigsaw piece 16 when they are joined together, the radially outer ring area having a circular shape and an uninterrupted and closed profile.

Figure 2A:
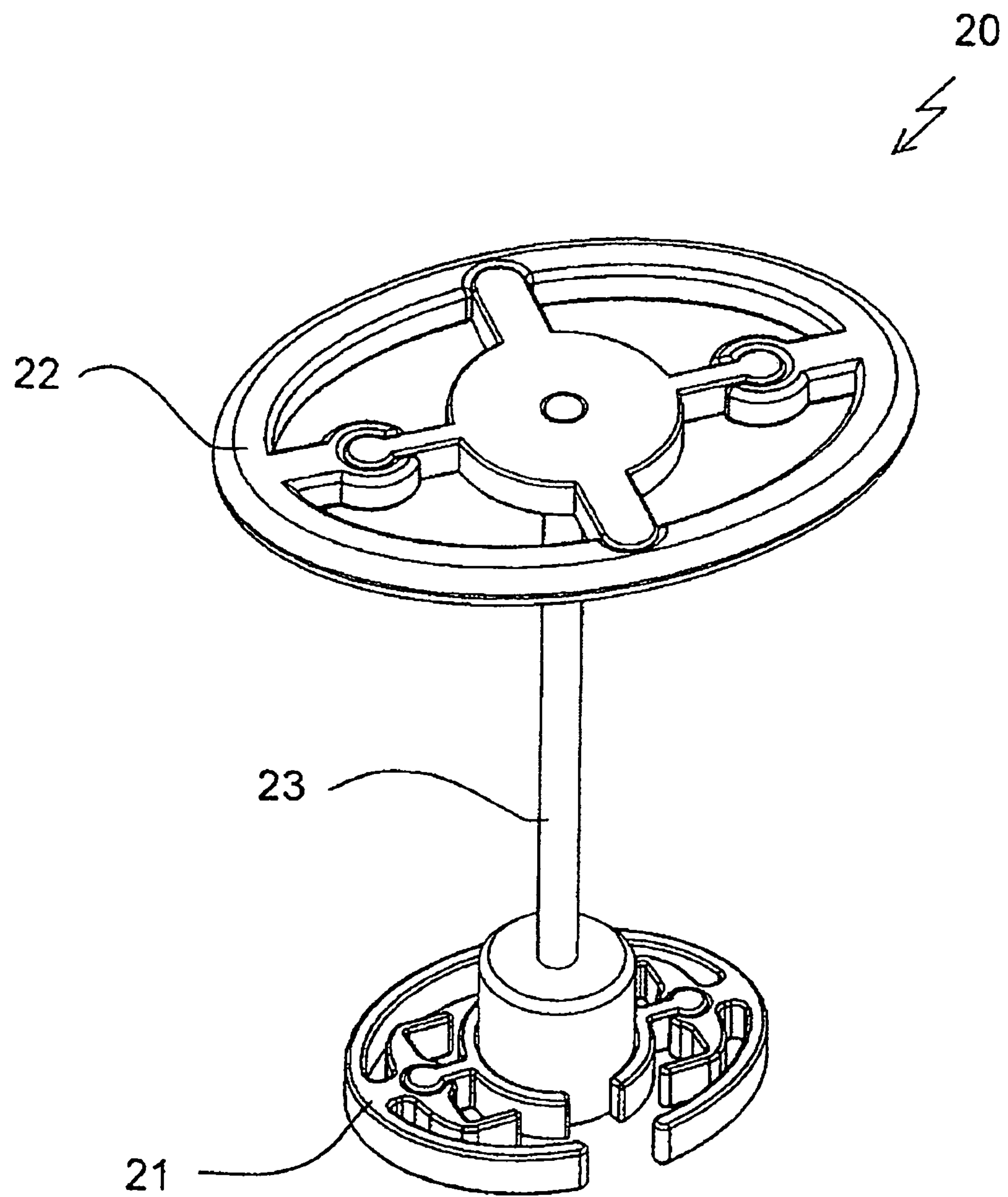
FIGS. 2*a-c* show an embodiment with two plate-shaped securing elements.
Figure 2B:
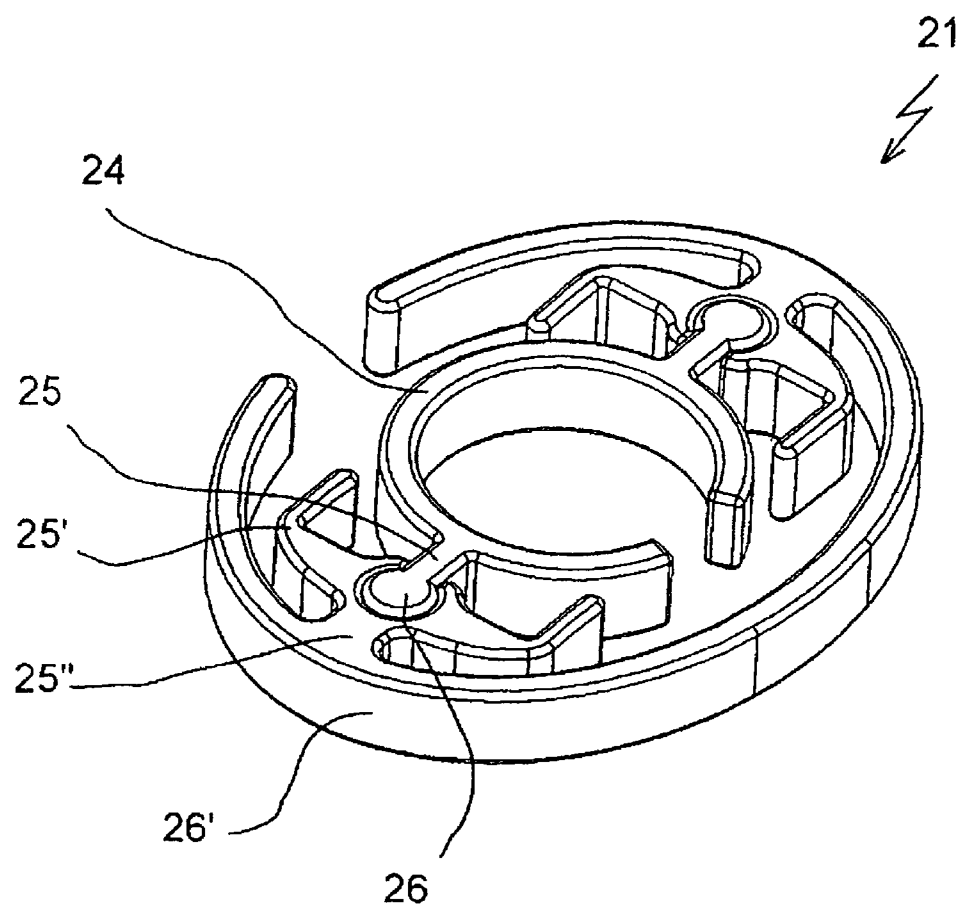
Figure 2C:
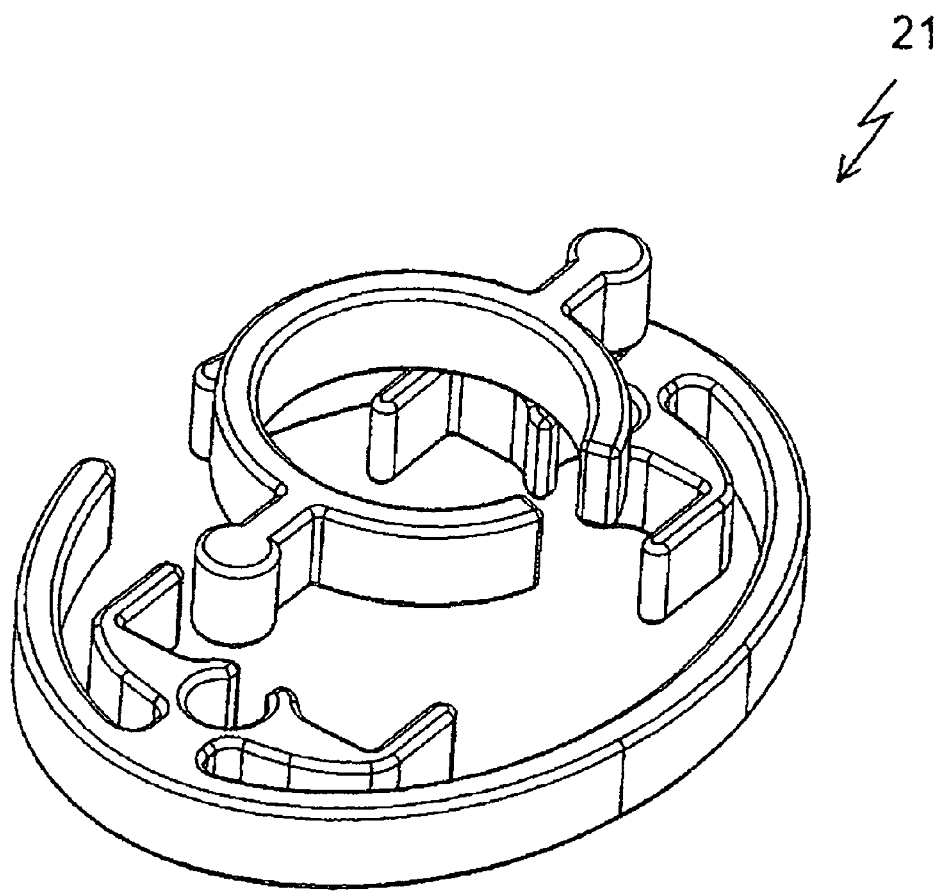

In the embodiment according to FIGS. 2*a-c* , both securing elements 21, 22 have a plate-shaped configuration and, according to the invention, are constructed from jigsaw pieces, wherein the first securing element 21 is designed to allow the auditory ossicle prosthesis 20 to bear on the footplate of the stirrup, while the second securing element 22 serves as a flat headplate for mechanical connection to the tympanic membrane. Since this constitutes a total prosthesis, the shaft-like connection element 23 is slightly longer than the short shaft 13 in FIG. 1*a*. In the first securing element 21 also, a radially inner jigsaw piece 26 containing the coupling area 24 is surrounded in a ring shape by a radially outer jigsaw piece 26', but both the radially inner ring area and also the radially outer ring area each have an interruption that increases the flexibility of the plate-shaped first securing element 21 when twisting in and out of the plane of the plate.

The embodiments in FIGS. 3*a* to 9*c* are distinguished by the fact that at least one jigsaw piece 36'; 46'; 56'; 66'; 76'; 86'; 96' is in each case provided that can be joined from the side onto at least one other jigsaw piece 36; 46; 56; 66; 76; 86; 96 at the outer edge of the plate-shaped first securing element 31; 41; 51; 61; 71; 81; 91. In the embodiments in FIGS. 3*a* to 7*c*, this jigsaw piece 36'; 46'; 56'; 66'; 76' that can be joined on from the side is shaped in each case as an appendix for the hammer or the manubrium of the auditory ossicle prosthesis 30; 40; 50; 60; 70 and, in the assembled state, protrudes radially outward from the edge of the plate-shaped first securing element 31; 41; 51; 61; 71.

Figure 3A:
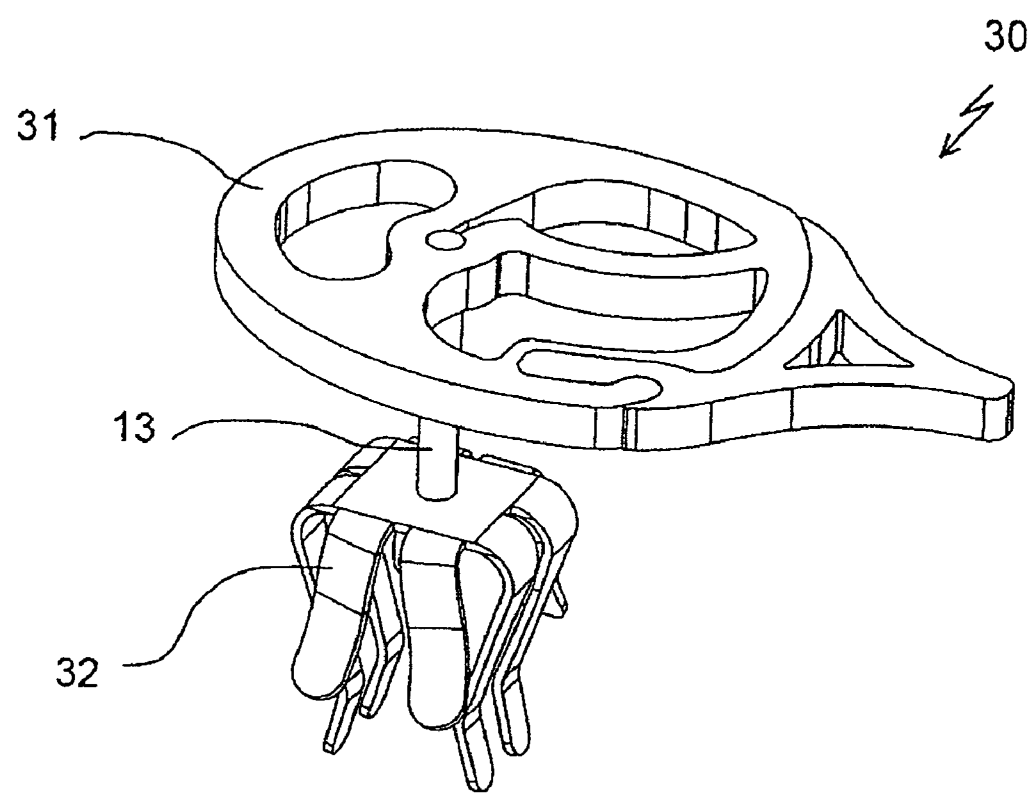
FIGS. 3*a-c* show an embodiment with a jigsaw piece which is shaped as an appendix for the hammer or the manubrium and can be joined to the first securing element from the side, and with a clip-shaped second securing element.
Figure 3B:
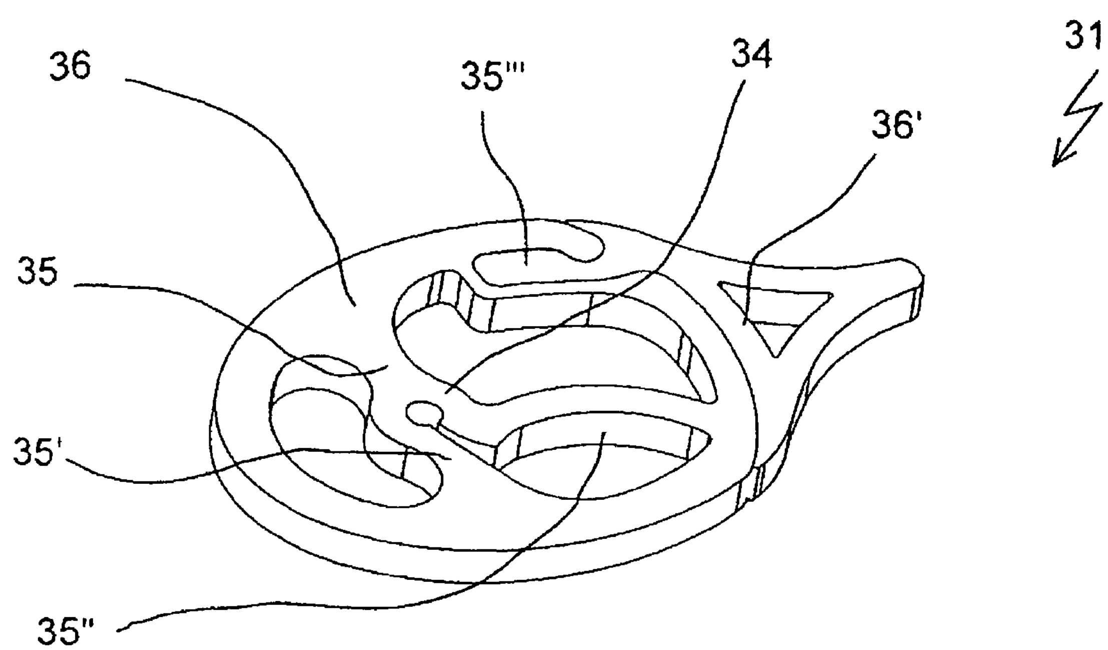
Figure 3C:
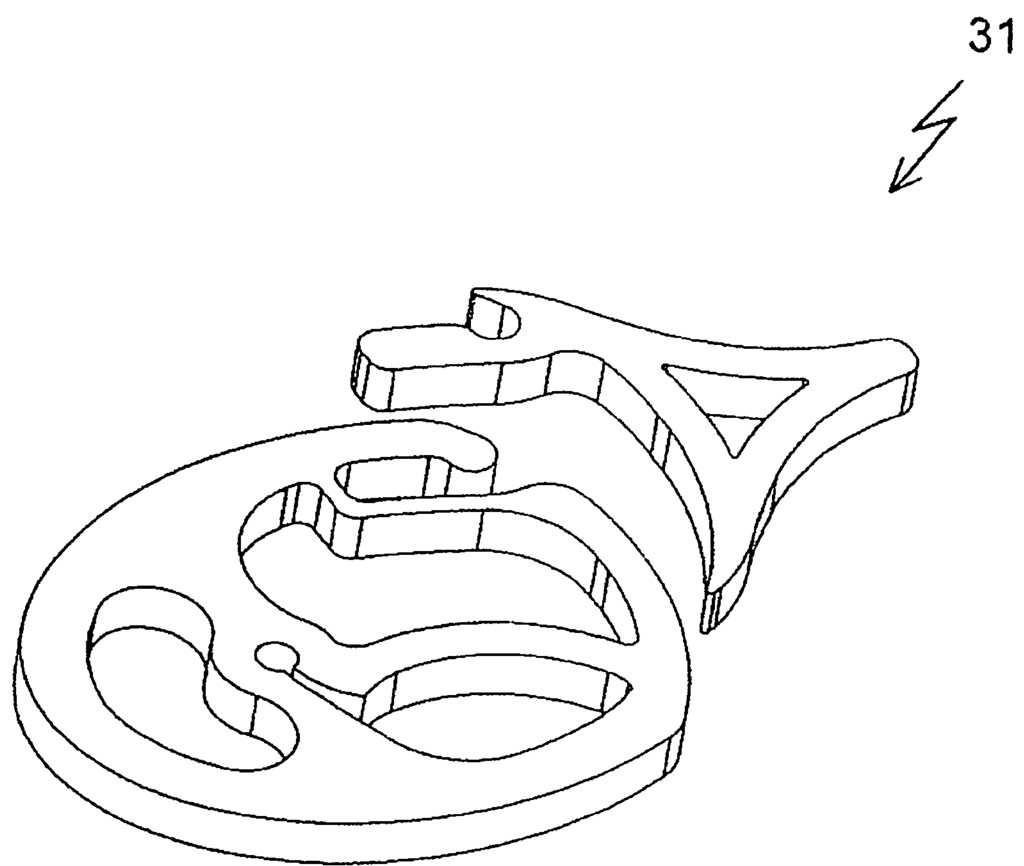

The second securing elements 32; 72 in the auditory ossicle prostheses 30; 70 according to FIGS. 3*a*; 7*a* are each designed as clips with several tongues, whereas in the embodiments according to FIGS. 4*a* to 6*a* they each have a slotted bell shape like the second securing element 12 in FIG. 1*a*.

Figure 4A:
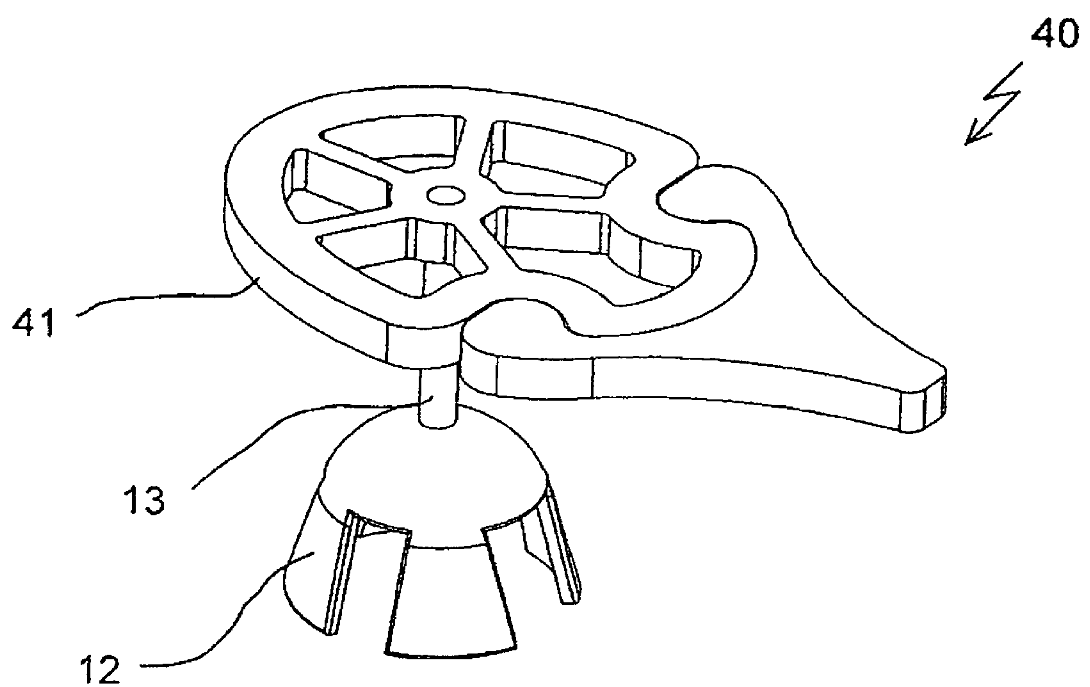
FIGS. 4*a-c* show an embodiment with a jigsaw piece that can be joined on from the side and with a radially outwardly extending bulge of the first securing element, after the jigsaw piece that can be joined on has been removed.
Figure 4B:
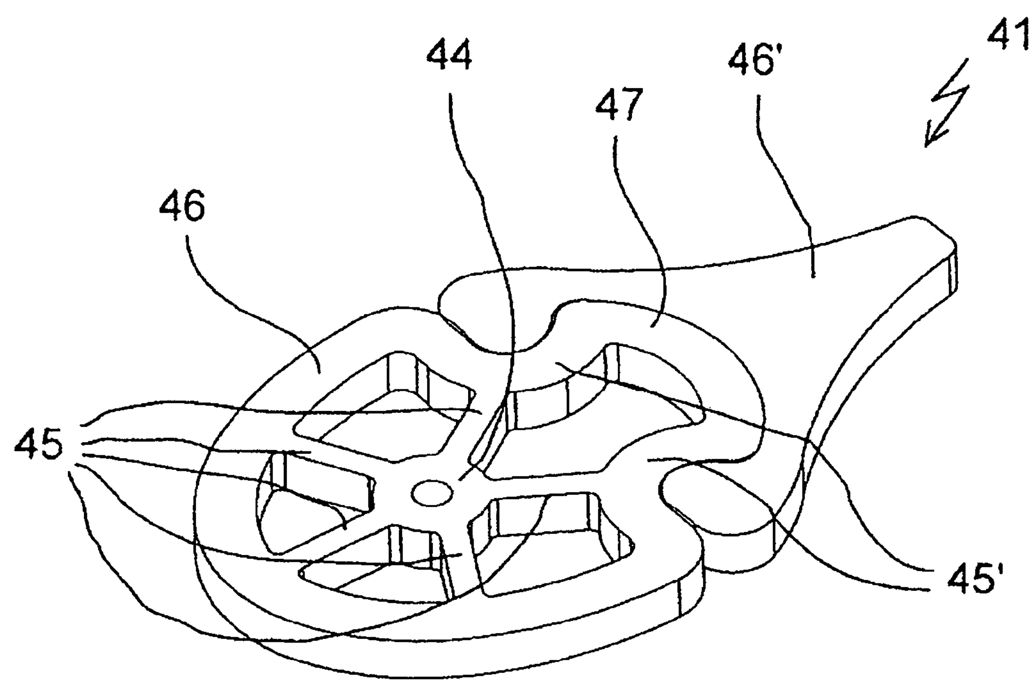
Figure 4C:
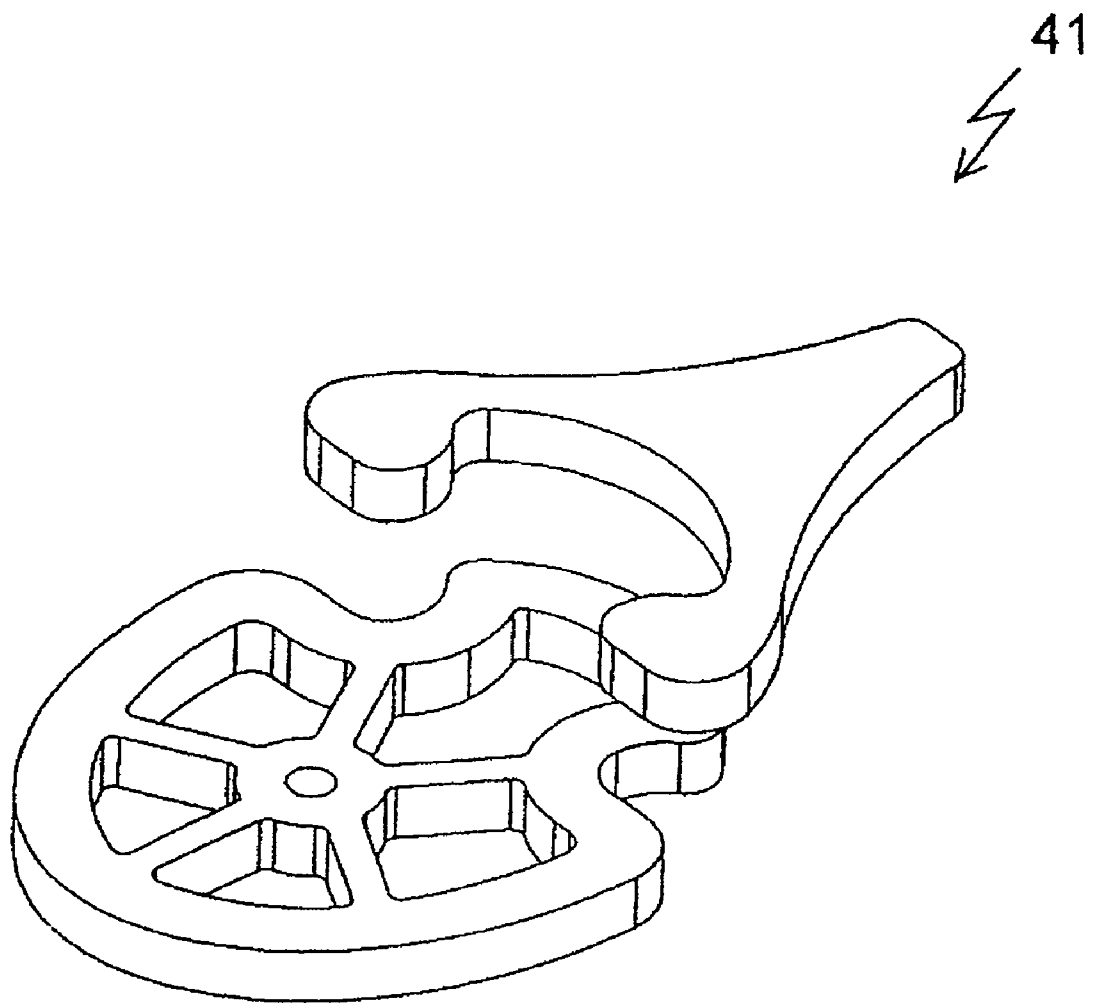
Figure 5A:
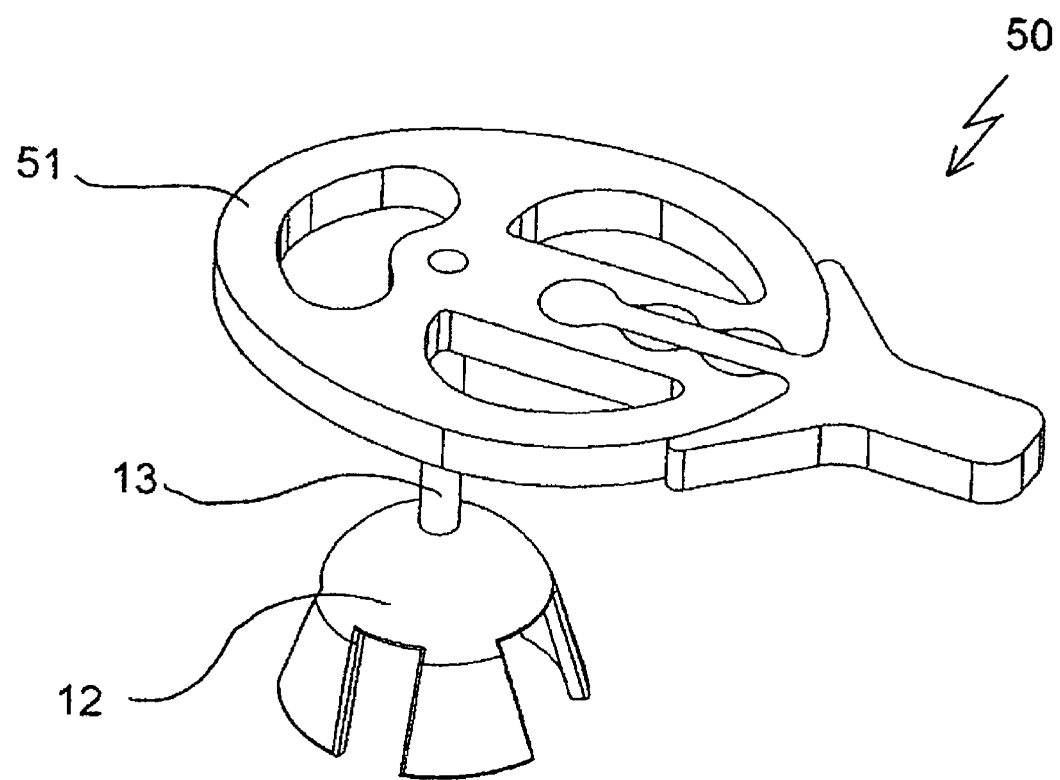
FIGS. 5*a-c* show an embodiment with a jigsaw piece that can be joined on from the side and that is anchored resiliently in the first securing-element.
Figure 5B:
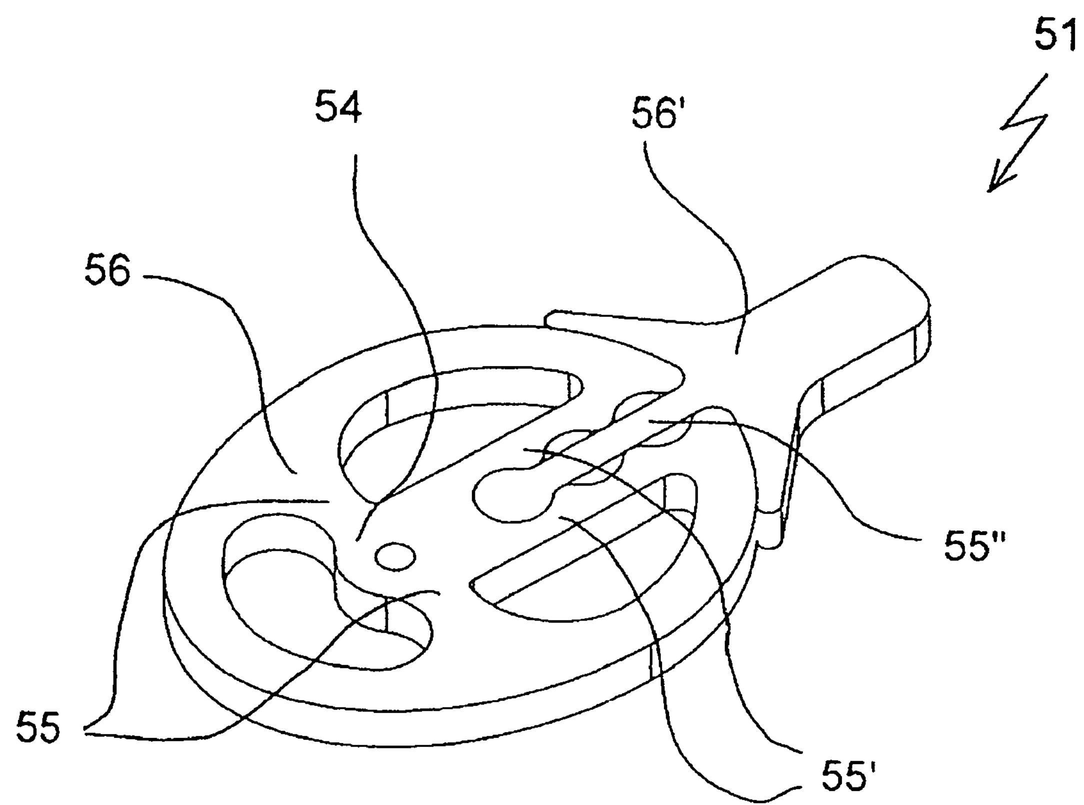
Figure 5C:
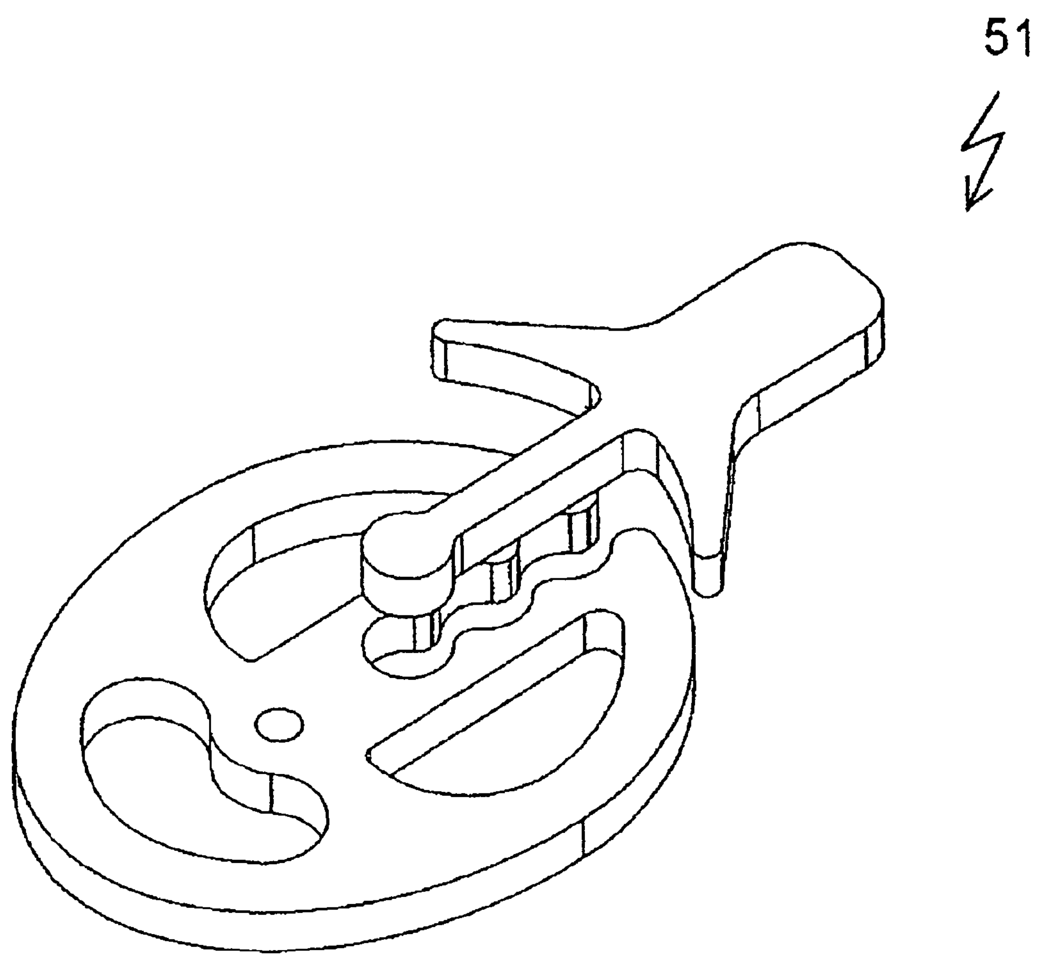

The plate-shaped first securing element 41 in the embodiment according to FIGS. 4*a-c* is distinguished by the fact that its first jigsaw piece 46 has, in the radially outer ring area, a bulge 47 which extends radially outward in the plane of the plate and which, even without the second jigsaw piece 46' joined on from the side, can serve as an appendix for the hammer or the manubrium of the auditory ossicle prosthesis 40.

In the first securing elements 51; 61; 71 of the auditory ossicle prostheses 50; 60; 70 according to FIGS. 5*a* to 7*c*, the jigsaw piece 56'; 66'; 76' that can be joined on from the side is in each case anchored resiliently in the first securing element 51; 61; 71.

The jigsaw pieces 66'; 76' that can be joined on in the embodiments according to FIGS. 6*a* to 7*c* can each be laterally anchored in the respective first jigsaw piece 66; 76 of the first securing element 61; 71 by means of a pair of web elements 65'; 75' designed as a clip element.

Figure 6A:
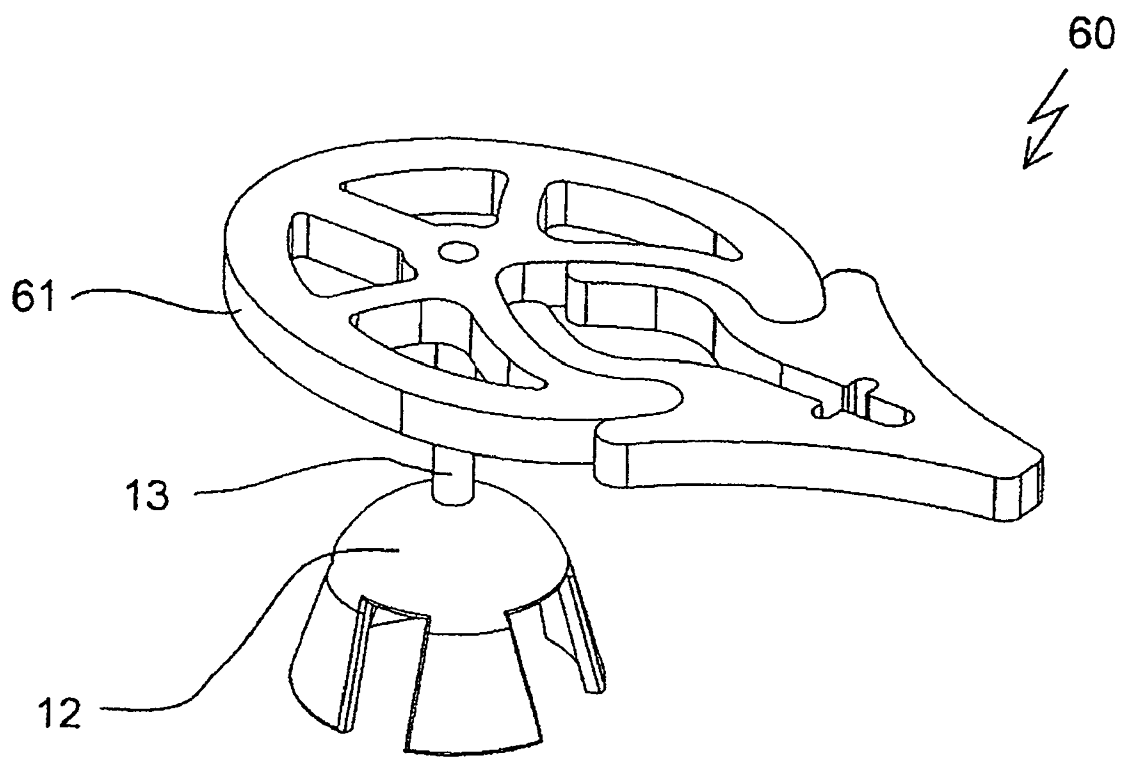
FIGS. 6*a-c* show an embodiment with a jigsaw piece that can be joined on from the side and that is anchored in the first securing element by means of a clip element.
Figure 6B:
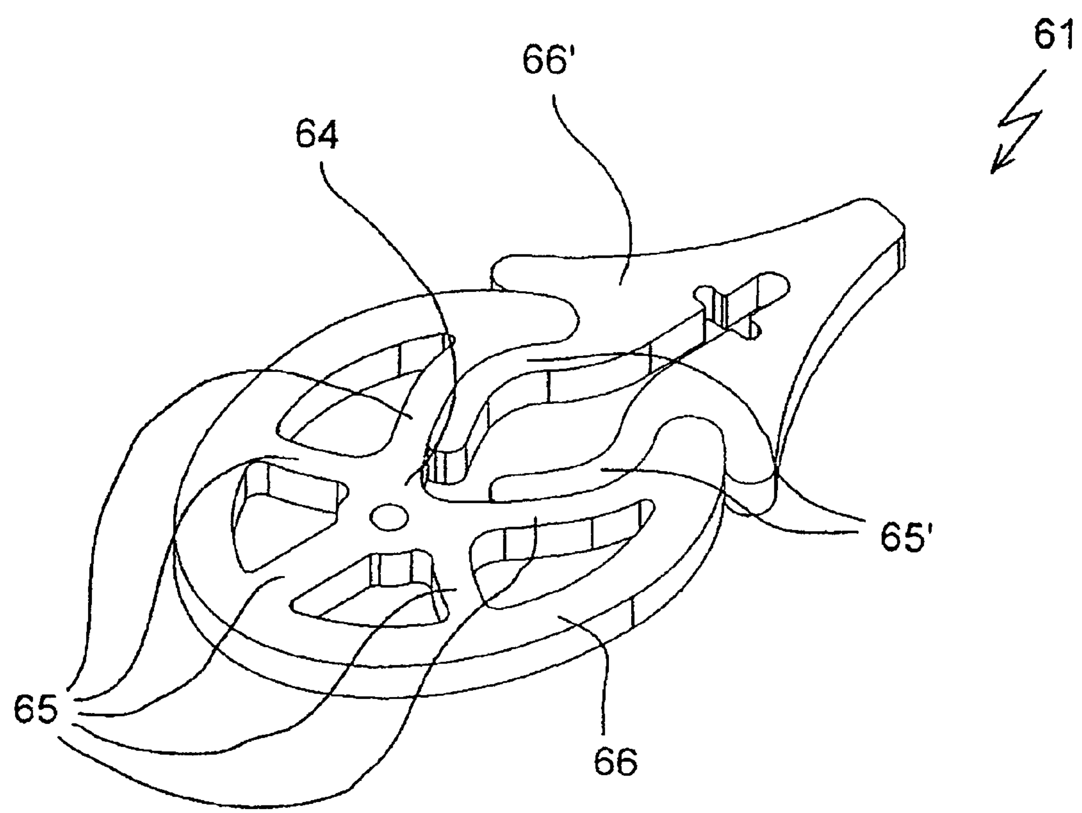
Figure 6C:
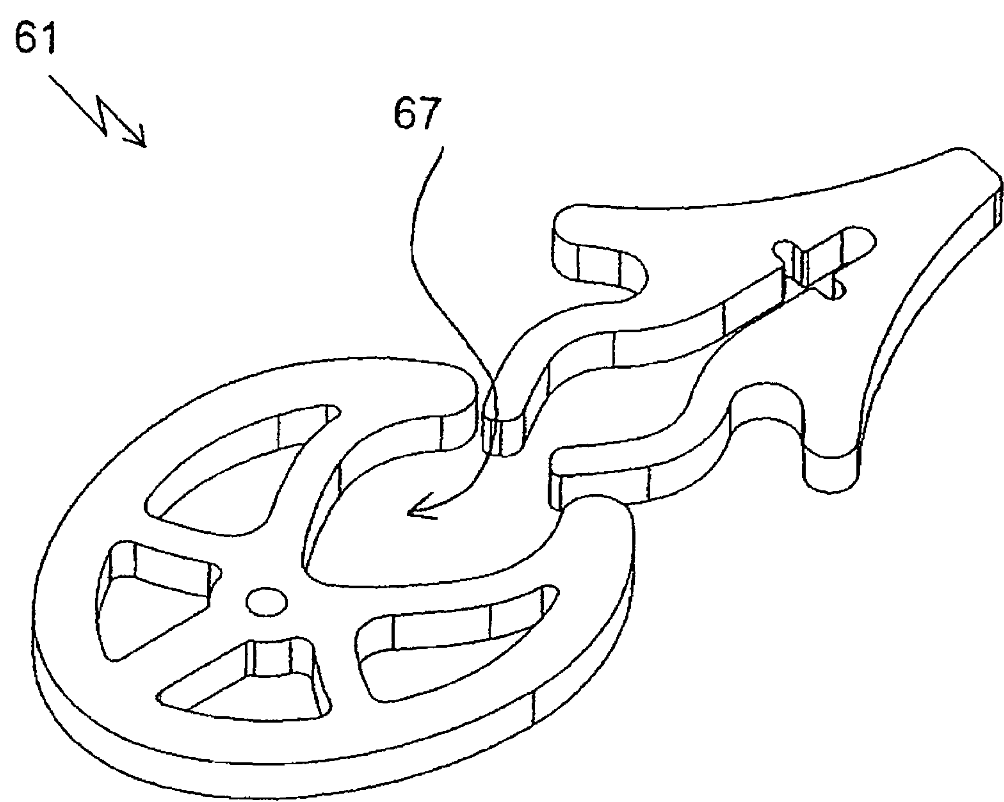

In the embodiment according to FIGS. 6*a-c*, the radially outer ring area of the first securing element 61 has a unilateral recess 67 for receiving the manubrium when the jigsaw piece 66' that can be joined on is not used.

Figure 7A:
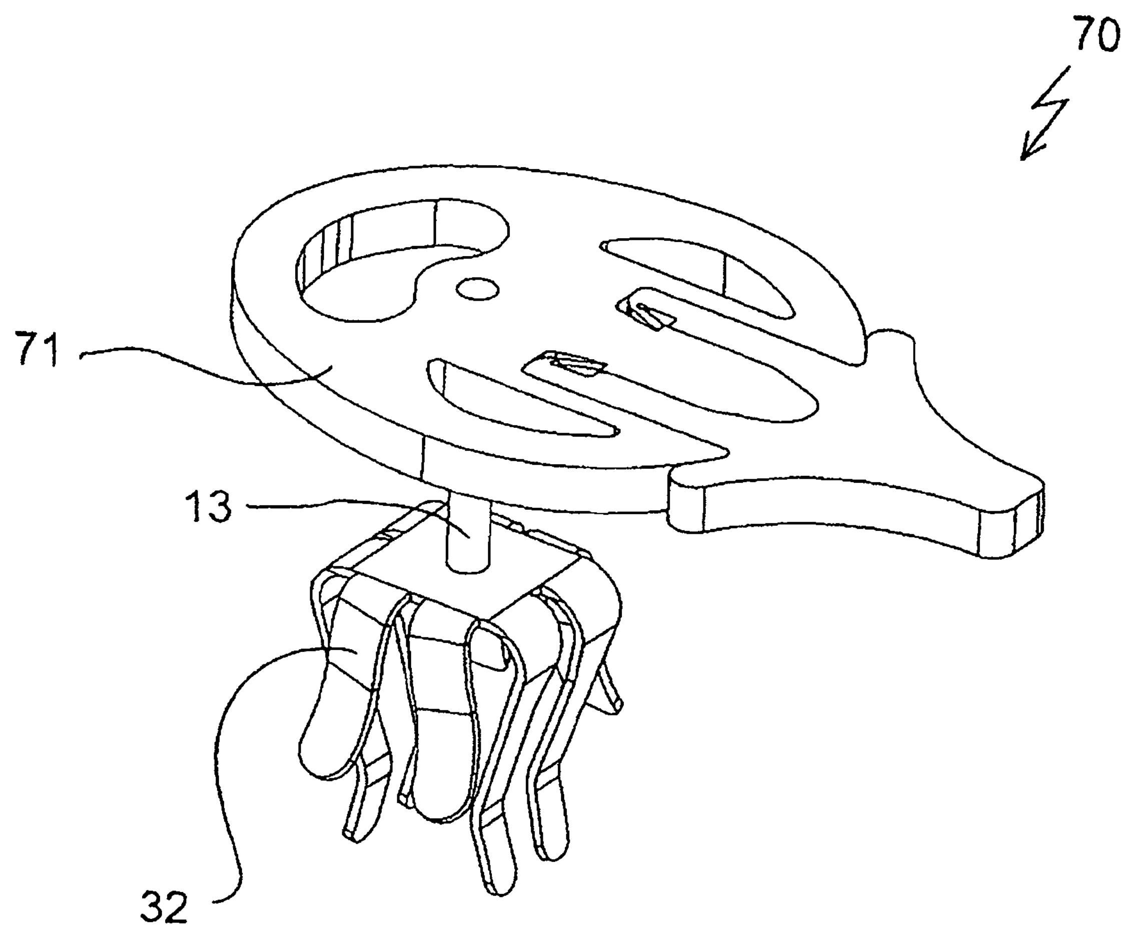
FIGS. 7*a-c* show an embodiment with a jigsaw piece that can be joined on from the side and that is anchored with a snap-fit action in the first securing element.
Figure 7B:
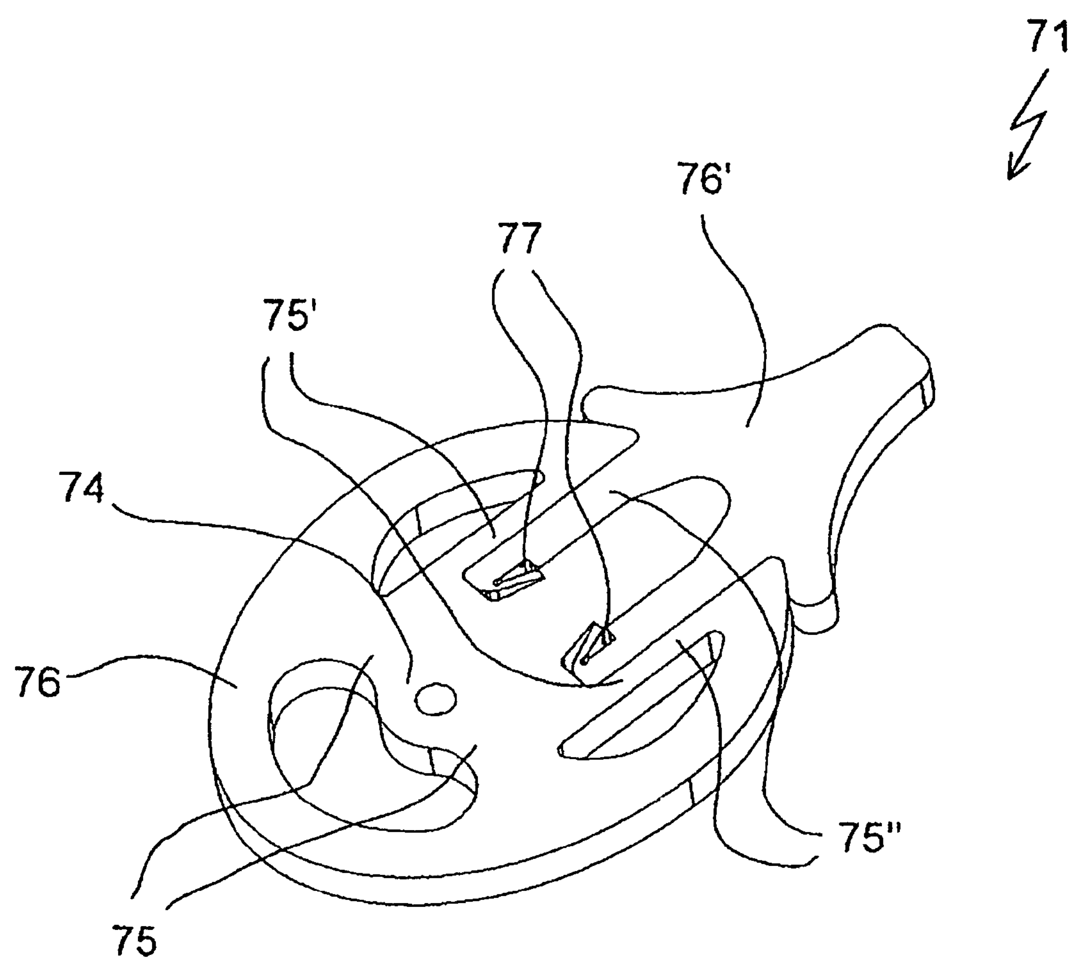
Figure 7C:
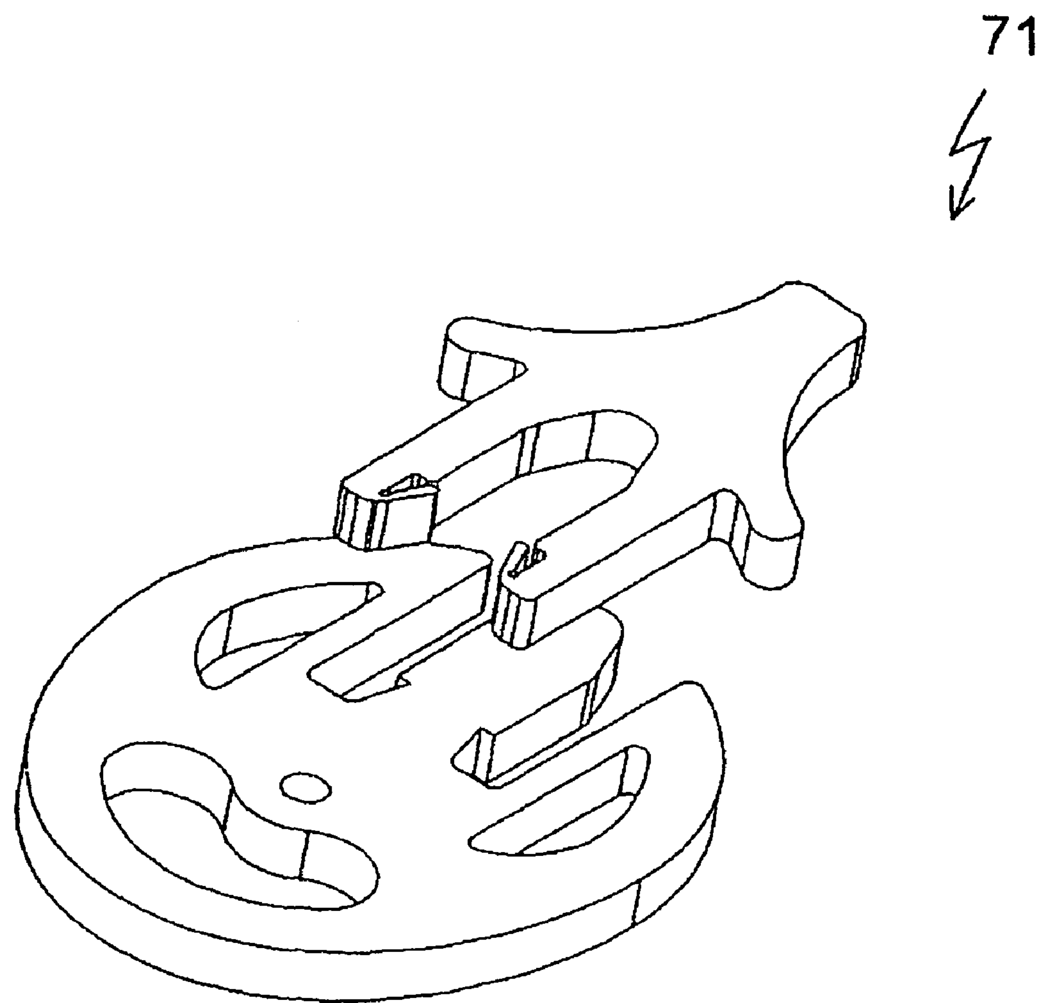

In the auditory ossicle prosthesis 70 according to FIGS. 7*a-c*, the jigsaw piece 76' that can be joined on from the side is anchored with a snap-fit action, and thus secure against loss, in the first securing element 71 by means of barbs 77 provided at the ends of the two web elements 75".

Figure 8A:
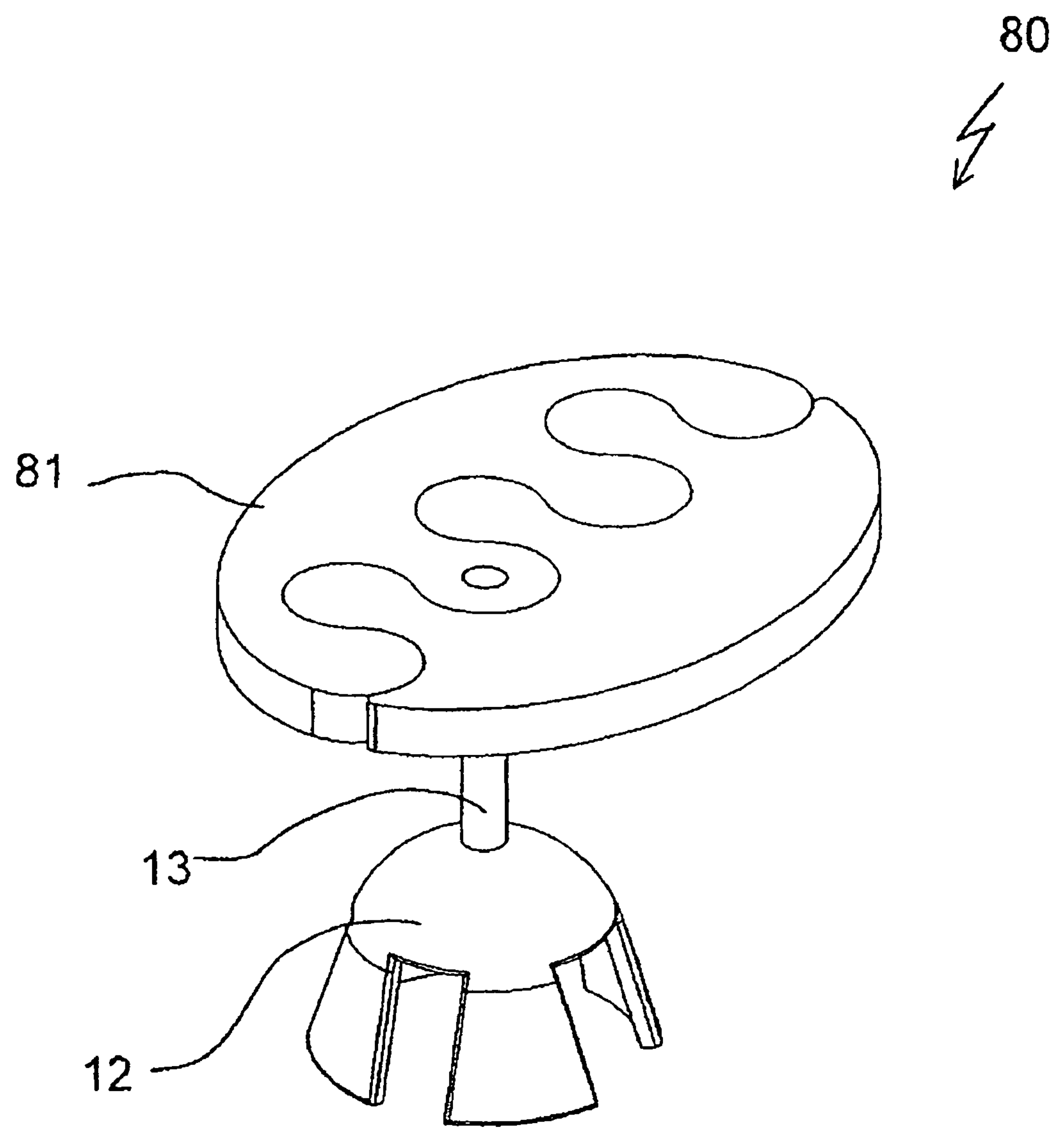
FIGS. 8*a-c* show an embodiment in which the plate-shaped first securing element, in the state with the jigsaw pieces joined together, forms an inherently closed surface and has no apertures extending through the plane of the plate.
Figure 8B:
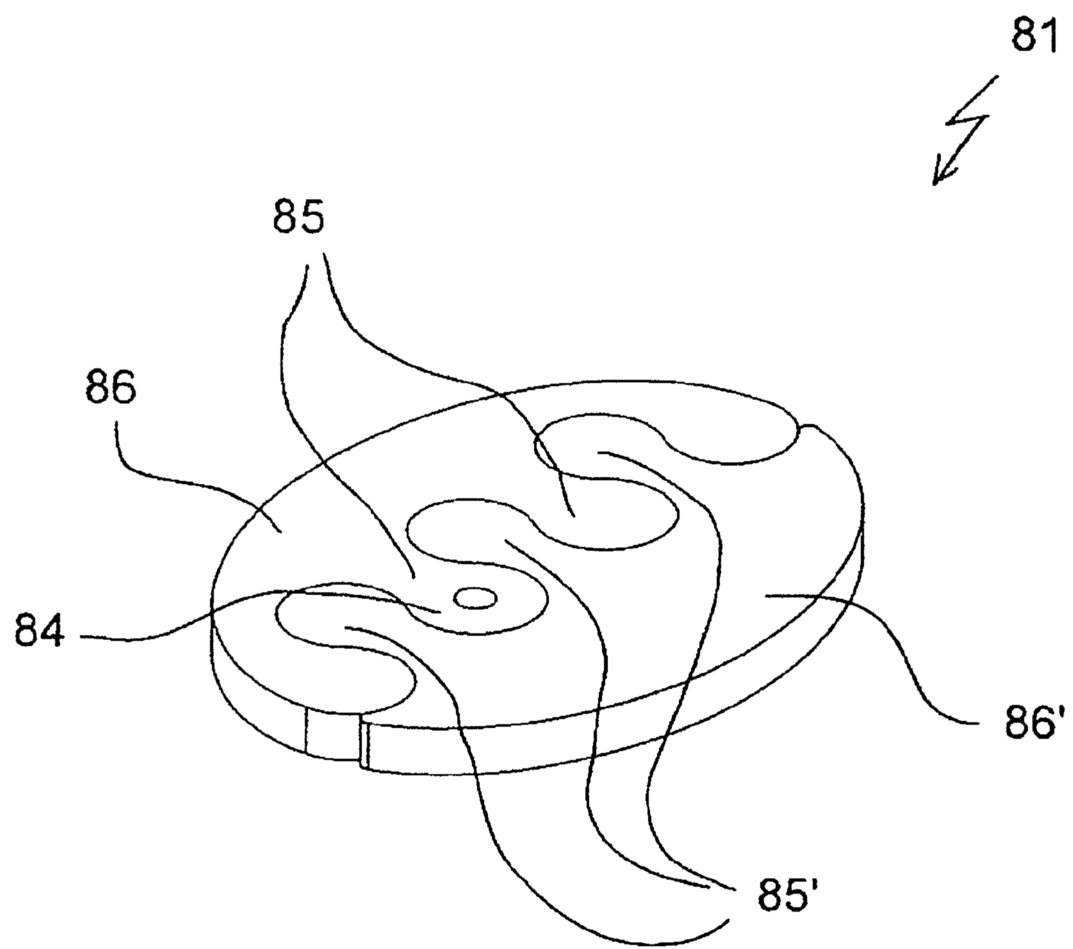
Figure 8C:
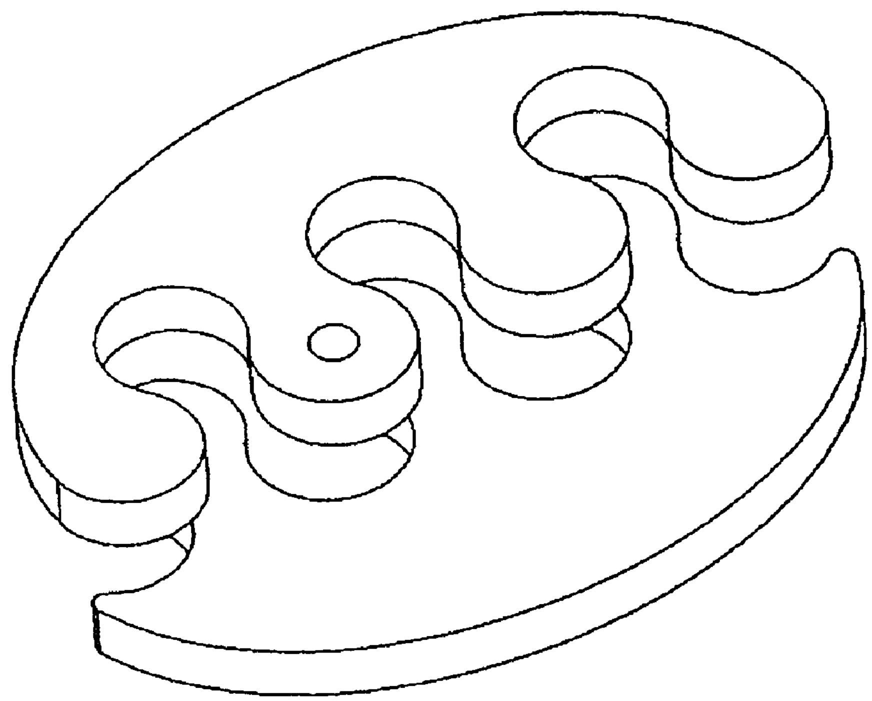

FIGS. 8*a-c* show an embodiment of the invention in which, in the state with the jigsaw pieces 86, 86' joined together, the plate-shaped first securing element 81 forms an inherently closed surface and has no apertures extending through the plane of the plate, as a result of which the plate is relatively stiff against twisting.

Figure 9A:
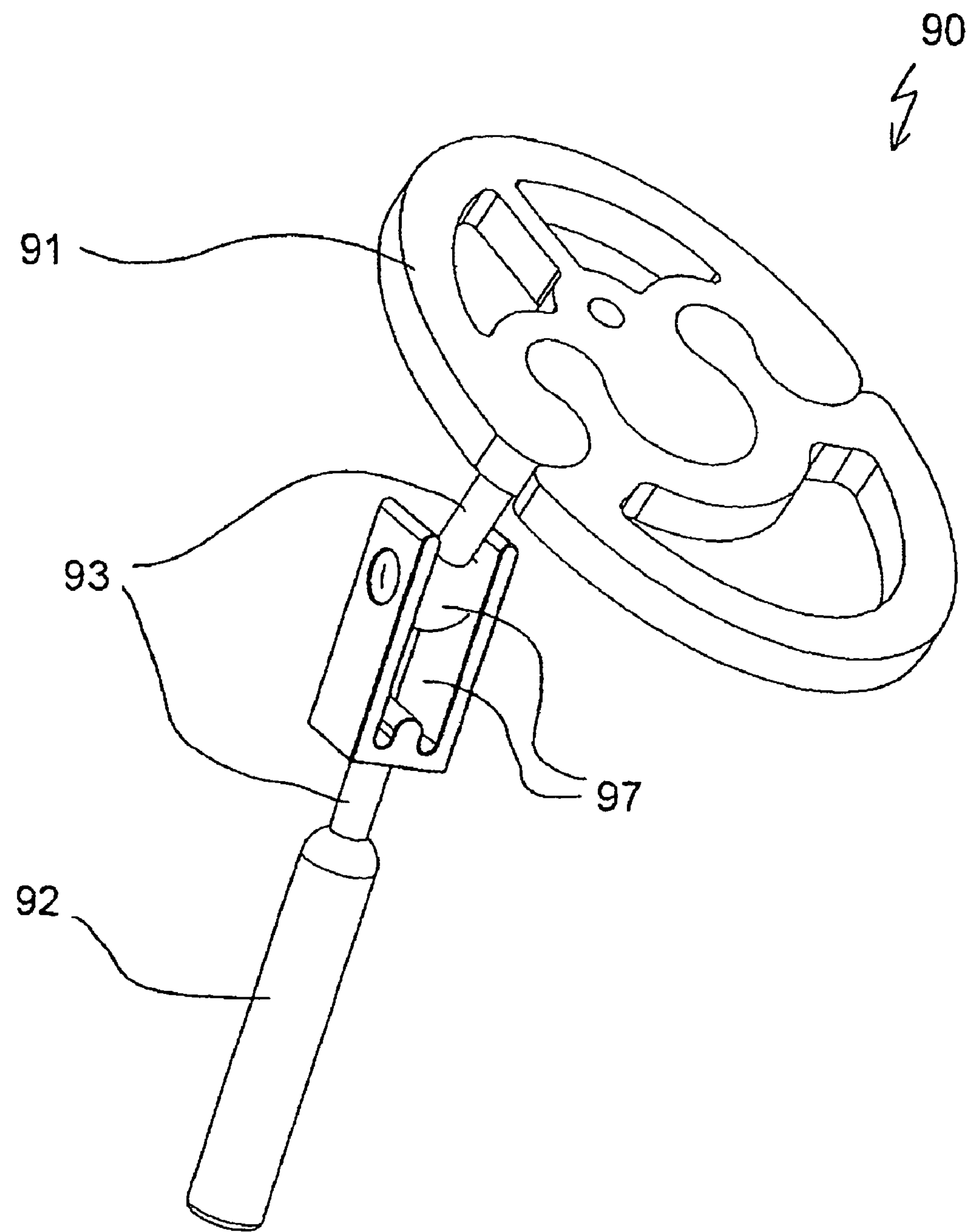
FIGS. 9*a-c* show an embodiment with a first securing element which is designed as a tympanic membrane headplate and has an annular structure, with a ball joint in the connection element, and with a second securing element shaped like a plunger.
Figure 9B:
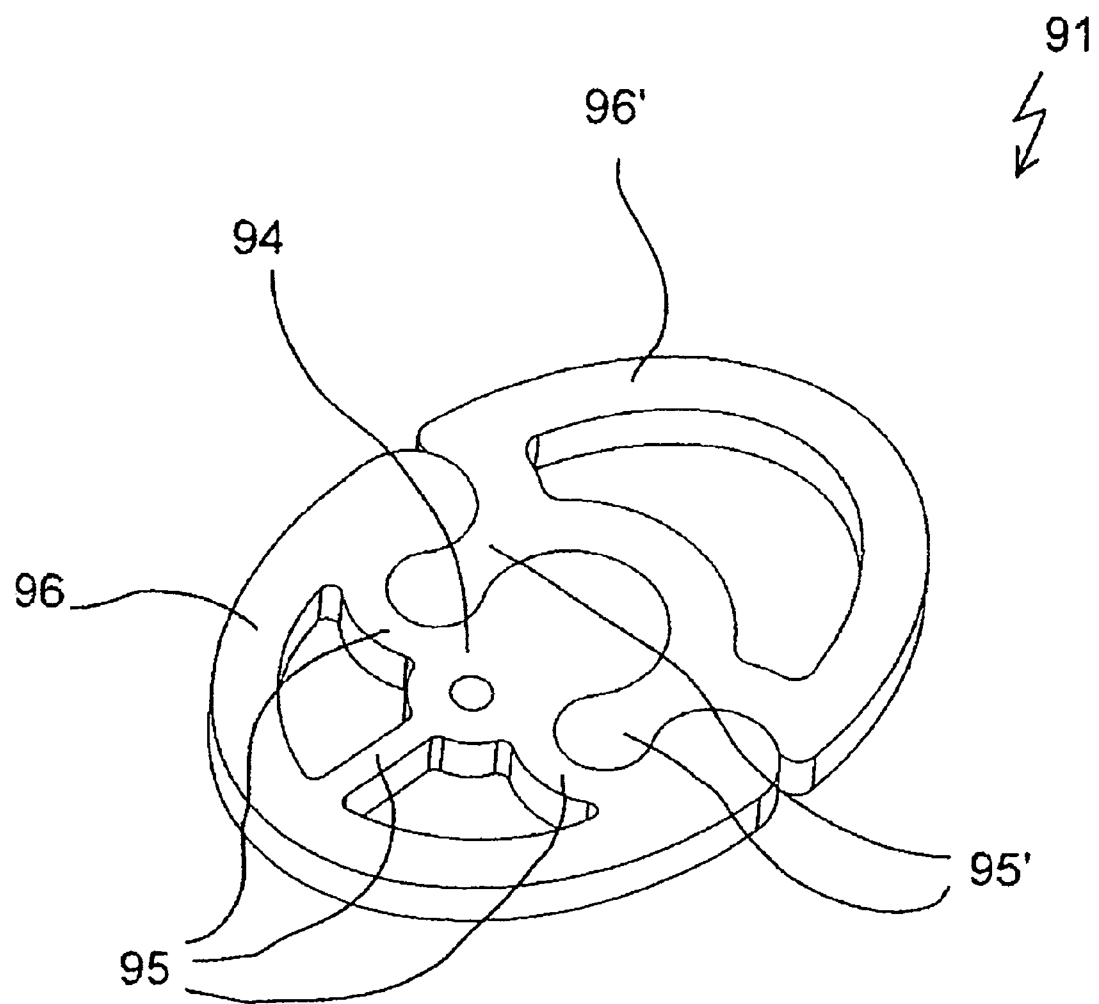
Figure 9C:
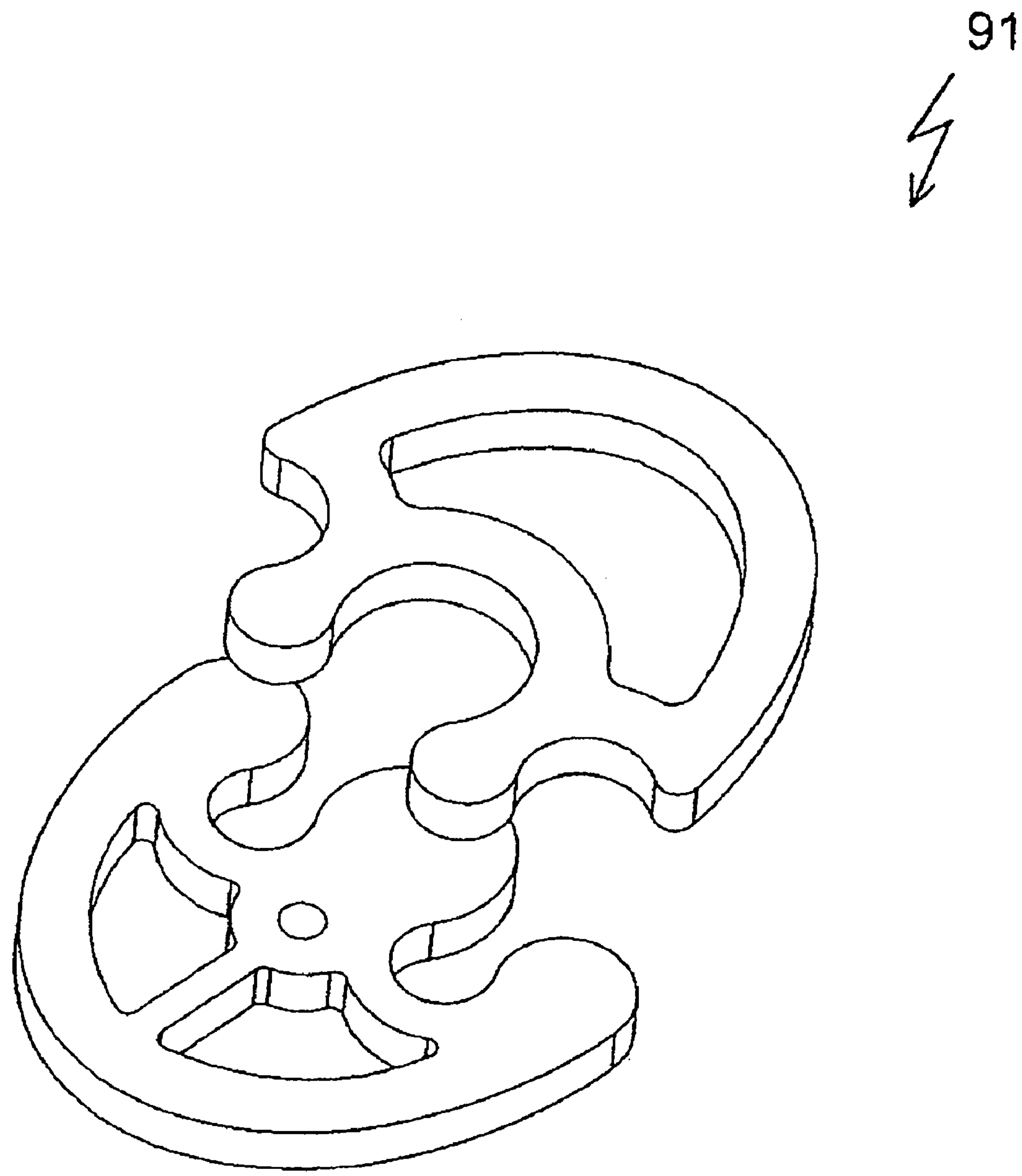

FIGS. 9*a-c*, finally, show an embodiment with a first securing element 91 again designed as a headplate for bearing on the tympanic membrane. In the present illustrative embodiment, the second securing element 92 at the end remote from the headplate in the auditory ossicle prosthesis 90 shown in FIG. 9*a* is designed as a plunger for direct coupling of the auditory ossicle prosthesis 90 to the inner ear. The shaft-shaped connection element 93 is here constructed in two parts and, between its two parts, has a ball joint 97 in order to increase the mechanical flexibility of the shaft.

The weight distribution of the individual parts of the auditory ossicle prosthesis 10; 20; 30; 40; 50; 60; 70; 80; 90 according to the invention can be calculated as a function of a desired, predefinable frequency response of the sound conduction in the middle ear, in such a way that individual tuning of the sound conduction properties is made possible.

In other embodiments of the auditory ossicle prosthesis according to the invention that are not specifically shown in the drawing, the central coupling areas and/or the web elements and/or the radial outer portions can also have other geometries in order to achieve the desired surface variability of the respective first securing element. For example, at least some of the web elements can have an interruption between the central coupling area and the radially outer portions. The radially outer portions can also be designed with one or more interruptions, can have an undulating outer contour and/or a unilateral recess for receiving the manubrium.

The invention claimed is:

1. An auditory ossicle prosthesis which replaces or spans at least one member or parts of one member of an ossicular chain, the auditory ossicle prosthesis comprising:

at one end, a substantially plate-shaped first securing element for bearing on a tympanic membrane or on a footplate of a stirrup, and, at its other end, a second securing element for mechanical connection to a member or parts of a member of an ossicular chain or to an inner ear, and also a connection element connecting the first and second securing elements to each other so as to conduct sound, and wherein the substantially plate-shaped first securing element has a radially inner coupling area mechanically coupling the substantially plate-shaped first securing element to the connection element, and also a plurality of web elements radially connecting the radially inner coupling area to at least one radially outer portion of the substantially plate-shaped first securing element, wherein the radially inner coupling area and/or the web elements and/or the at least one radially outer portion are of such a geometric configuration that they together form jigsaw pieces of a jigsaw puzzle from which the substantially plate-shaped first securing element can be assembled in its entirety with the pieces of the jigsaw puzzle being non-rotatable relative to each other, wherein the jigsaw pieces can be joined to one another or removed from one another, and wherein the substantially plate-shaped first securing element is inherently mechanically stable in a state with the jigsaw pieces joined together.

2. The auditory ossicle prosthesis according to claim 1, wherein both the first and the second securing elements are plate-shaped and are constructed from the jigsaw pieces, wherein the substantially plate-shaped first securing element comprises a flat headplate for mechanical connection to the tympanic membrane, and the second securing element is designed to allow the auditory ossicle prosthesis to bear on the footplate of the stirrup.

3. The auditory ossicle prosthesis according to claim 1, wherein the radially inner coupling area comprises at least one radially inner jigsaw piece and the at least one radially outer portion comprises at least one radially outer jigsaw piece, with the at least one radially outer jigsaw piece forming a ring that surrounds the radially inner jigsaw piece when the radially inner coupling area, the web elements and the at least one radially outer portion are connected together.

4. The auditory ossicle prosthesis according to claim 1, wherein at least a first one of the jigsaw pieces is provided that can be joined from a side thereof onto at least a second one of the jigsaw pieces at the outer edge of the substantially plate-shaped first securing element.

5. The auditory ossicle prosthesis according to claim 4, wherein the first one of the jigsaw pieces that can be joined from the side thereof is shaped as an appendix for a hammer or a manubrium of the auditory ossicle prosthesis and, when the radially inner coupling area, the web elements and the at least one radially outer portion are connected together, protrudes radially outward from the outer edge of the substantially plate-shaped first securing element.

6. The auditory ossicle prosthesis according to claim 4, wherein the first one of the jigsaw pieces that can be joined from the side is anchored resiliently in the substantially plate-shaped first securing element.

7. The auditory ossicle prosthesis according to claim 6, wherein the first one of the jigsaw pieces that can be joined from the side is anchored in the substantially plate-shaped first securing element by a clip element.

8. The auditory ossicle prosthesis according to claim 4, wherein the first one of the jigsaw pieces that can be joined from the side is anchored with a snap-fit action in the substantially plate-shaped first securing element.

9. The auditory ossicle prosthesis according to claim 1, wherein, when the radially inner coupling area, the web elements and the at least one radially outer portion are connected together, the substantially plate-shaped first securing element has apertures extending through a plane in which the substantially plate-shaped first securing element is disposed.

10. The auditory ossicle prosthesis according to claim 1, wherein, when the radially inner coupling area, the web elements and the at least one radially outer portion are connected together, the substantially plate-shaped first securing element forms an inherently closed surface and has no apertures extending through a plane in which the substantially plate-shaped first securing element is disposed.

11. The auditory ossicle prosthesis according to claim 1, wherein the at least one radially outer portion of the substantially plate-shaped first securing element forms an outer ring area.

12. The auditory ossicle prosthesis according to claim 11, wherein the outer ring area of the substantially plate-shaped first securing element is uninterrupted and closed.

13. The auditory ossicle prosthesis according to claim 11, wherein the outer ring area of the substantially plate-shaped first securing element has at least one interruption.

14. The auditory ossicle prosthesis according to claim 11, wherein the outer ring area of the substantially plate-shaped first securing element has an oval or circular shape.

15. The auditory ossicle prosthesis according to claim 11, wherein the outer ring area of the substantially plate-shaped first securing element has a bulge extending radially outwardly in a plane in which the substantially plate-shaped first securing element is disposed.

16. The auditory ossicle prosthesis according to claim 11, wherein the outer ring area of the substantially plate-shaped first securing element has a unilateral recess for receiving a manubrium.

17. The auditory ossicle prosthesis according to claim 11, wherein the outer ring area has an undulating outer contour.

18. The auditory ossicle prosthesis according to claim 1, wherein the web elements between the radially inner coupling area and the at least one radially outer portion of the substantially plate-shaped first securing element are uninterrupted.

19. The auditory ossicle prosthesis according to claim 1, wherein at least one of the web elements has an interruption between the radially inner coupling area and the at least one radially outer portion of the substantially plate-shaped first securing element.

20. The auditory ossicle prosthesis according to claim 1, wherein the web elements of the substantially plate-shaped first securing element are not rectilinear in a plane in which the substantially plate-shaped first securing element is disposed, but instead extend along curved paths within the plane.

21. The auditory ossicle prosthesis according to claim 1, wherein each web element is connected to at least two other web elements.

22. The auditory ossicle prosthesis according to claim 1, wherein the radially inner coupling area is arranged centrally around an area centroid of the substantially plate-shaped first securing element.

23. The auditory ossicle prosthesis of claim 1, wherein one of the jigsaw puzzle pieces includes a bulbous projection configured to be received within a correspondingly shaped bulbous receptacle of the other of the jigsaw puzzle pieces.

24. An auditory ossicle prosthesis which replaces or spans at least one member or parts of one member of an ossicular chain, said auditory ossicle prosthesis comprising:

a substantially plate-shaped first securing element defining one end of said auditory ossicle prosthesis for bearing on a tympanic membrane or on a footplate of a stirrup, said first securing element comprising a radially inner coupling area, a radially outer portion and a plurality of web elements radially connecting said inner coupling area to said outer portion;

a second securing element defining an opposite end of said auditory ossicle prosthesis for mechanical connection to a member or parts of a member of an ossicular chain or to an inner ear; and a connection element interconnecting said first and second securing elements to one another so as to conduct sound, said connection element being mechanically coupled to said first securing element by said inner coupling area;

wherein at least two of: said inner coupling area; one of said web elements; and said outer portion of said first securing element define respective independent and discrete first and second jigsaw puzzle pieces from which said first securing element can be assembled in its entirety, said first and second jigsaw puzzle pieces defining respective complementary geometric portions disposed in interlocking but releasable engagement with one another, an overall shape of said first securing element being variable before or during implantation of said auditory ossicle prosthesis within an ossicular chain by disengaging said first jigsaw puzzle piece from said second jigsaw puzzle piece or by engaging said first jigsaw puzzle piece with said second jigsaw puzzle piece.

25. The auditory ossicle prosthesis of claim 24, wherein said geometric portion of said first jigsaw puzzle piece defines a bulbous projection and said geometric portion of said second jigsaw puzzle piece defines a bulbous receptacle which receives said bulbous projection to interlock said first and second jigsaw puzzle pieces with one another.

26. The auditory ossicle prosthesis of claim 24, wherein top surfaces of the first and second jigsaw puzzle pieces are co-planar and together form a top plane of the first securing element and bottom surfaces of the first and second jigsaw puzzle pieces are opposite the top surfaces of the first and second jigsaw puzzle pieces, the bottom surfaces being co-planar and together forming a bottom plane of the first securing element, and the first and second jigsaw puzzle pieces interlock with one another entirely within an area located between the top plane and the bottom plane of the first securing element.

27. The auditory ossicle prosthesis of claim 26, wherein said geometric portion of said first jigsaw puzzle piece defines a projection and said geometric portion of said second jigsaw puzzle piece defines a receptacle which receives said projection to interlock said first and second jigsaw puzzle pieces with one another.

28. The auditory ossicle prosthesis of claim 24, wherein said first and second jigsaw puzzle pieces are non-rotatable relative to one another when interlocked with one another.

29. The auditory ossicle prosthesis of claim 24, wherein an outer circumferential surface of the first jigsaw puzzle piece is non-circular.

30. The auditory ossicle prosthesis of claim 24, wherein the first jigsaw puzzle piece and the second jigsaw puzzle piece engage along a first direction of movement, and the first jigsaw puzzle piece and the second jigsaw puzzle piece are prevented from moving relative to each other only in a second direction perpendicular to the first direction when the first jigsaw puzzle piece and the second jigsaw puzzle piece are engaged.

* * * * *